(12) United States Patent
Kaeseberg et al.

(10) Patent No.: US 11,826,109 B2
(45) Date of Patent: Nov. 28, 2023

(54) TECHNIQUE FOR GUIDING ACQUISITION OF ONE OR MORE REGISTRATION POINTS ON A PATIENT'S BODY

(71) Applicant: Stryker European Operations Limited, Carrigtwohill (IE)

(72) Inventors: Marc Kaeseberg, Biesenthal (DE); Christian Winne, Berlin (DE); Christopher Özbek, Berlin (DE)

(73) Assignee: Stryker European Operations Limited, Carrigtwohill (IE)

(*) Notice: Subject to any disclaimer, the term of this patent is extended or adjusted under 35 U.S.C. 154(b) by 54 days.

(21) Appl. No.: 17/476,620

(22) Filed: Sep. 16, 2021

(65) Prior Publication Data
US 2022/0087750 A1  Mar. 24, 2022

(30) Foreign Application Priority Data

Sep. 24, 2020 (EP) .................................... 20198095

(51) Int. Cl.
*A61B 34/20* (2016.01)
*A61B 90/00* (2016.01)
*G06T 7/00* (2017.01)

(52) U.S. Cl.
CPC ............ *A61B 34/20* (2016.02); *A61B 90/361* (2016.02); *G06T 7/0012* (2013.01);
(Continued)

(58) Field of Classification Search
CPC . G06T 2207/30008; G06T 2207/30088; G06T 2207/30204; G06T 7/0012;
(Continued)

(56) References Cited

U.S. PATENT DOCUMENTS

| 6,560,354 B1* | 5/2003 | Maurer, Jr. ............... G06T 7/33 382/173 |
| 7,194,295 B2 | 3/2007 | Vilsmeier |

(Continued)

FOREIGN PATENT DOCUMENTS

| CA | 2776952 A1 | 4/2011 |
| EP | 3493161 A2 | 6/2019 |

(Continued)

OTHER PUBLICATIONS

Math Works section Image Registration with Control Point Registration internet access https://www.mathworks.com/help/images/control-point-registration.html dated access Sep. 16, 2017 using wayback machine (Year: 2017).*
(Continued)

*Primary Examiner* — Serkan Akar
*Assistant Examiner* — Patrick M Mehl
(74) *Attorney, Agent, or Firm* — Howard & Howard Attorneys PLLC

(57) ABSTRACT

A computer-implemented method for guiding a surgeon to acquire one or more registration points on a body of a patient. The method includes matching a non-patient-specific virtual mask to image data of a patient, and obtaining a plurality of image surface points defining a skin surface in the image data. The method further comprises determining, based on the matched virtual mask, for at least one of the plurality of image surface points, a priority value indicative of a priority for acquiring a registration point at a position, relative to the patient's body, that corresponds to a position of the at least one image surface point relative to the skin surface defined in the image data. The method also includes triggering display of a visualization of the priority value, or of a visualization of information derived from the priority value.

19 Claims, 11 Drawing Sheets

(52) U.S. Cl.
CPC . *A61B 2034/2068* (2016.02); *A61B 2090/363* (2016.02); *G06T 2207/30008* (2013.01); *G06T 2207/30088* (2013.01); *G06T 2207/30204* (2013.01)

(58) Field of Classification Search
CPC ...... A61B 2034/2068; A61B 2090/363; A61B 34/20; A61B 90/361
See application file for complete search history.

(56) References Cited

U.S. PATENT DOCUMENTS

| | | |
|---|---|---|
| 10,403,009 B2 | 9/2019 | Mariampillai et al. |
| 10,470,825 B2 | 11/2019 | Gallop et al. |
| 2011/0002523 A1 | 1/2011 | Prakash et al. |
| 2014/0316234 A1 | 10/2014 | Waite et al. |
| 2018/0046875 A1 | 2/2018 | Caluser |
| 2019/0231433 A1 | 8/2019 | Amanatullah |
| 2020/0015895 A1 | 1/2020 | Frielinghaus et al. |
| 2021/0059764 A1* | 3/2021 | Rafii-Tari ............... A61B 1/044 |
| 2021/0241480 A1* | 8/2021 | Kämäräinen ........ A61B 5/1077 |

FOREIGN PATENT DOCUMENTS

| | | |
|---|---|---|
| WO | 201790210 A1 | 6/2017 |
| WO | 2017190210 A1 | 11/2017 |
| WO | 2018162079 A1 | 9/2018 |
| WO | 2021030629 A1 | 2/2021 |

OTHER PUBLICATIONS

Guan et al. Chin. J. Mech. Eng. (2018) 31:76 16 pages (Year: 2018).*

Yao, Xu et al., "Advances on Pancreas Segmentation: a Review", Multimedia Tools and Applications, Kluwer Academic Publishers, Boston, vol. 79, No. 9-10, Dec. 18, 2019, pp. 6799-6821.

* cited by examiner

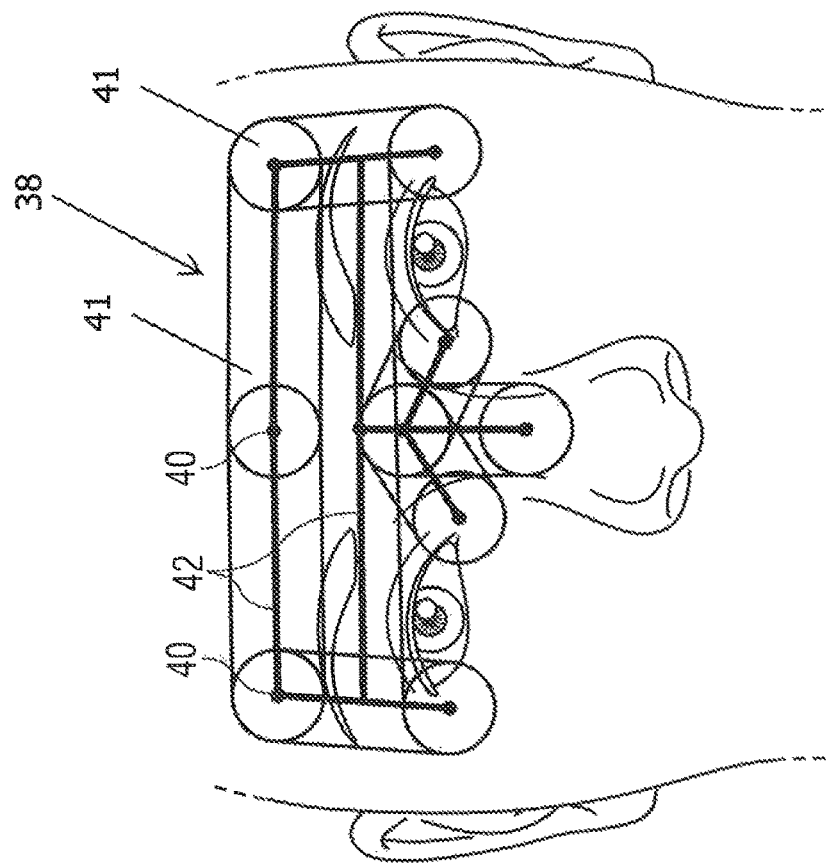
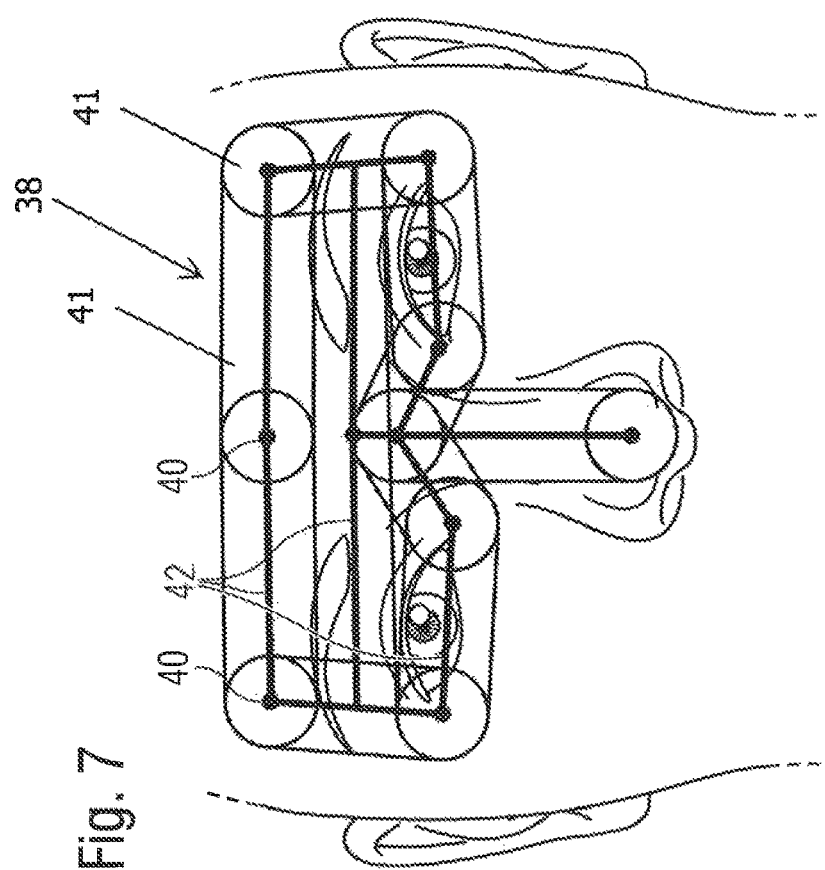
Fig. 7

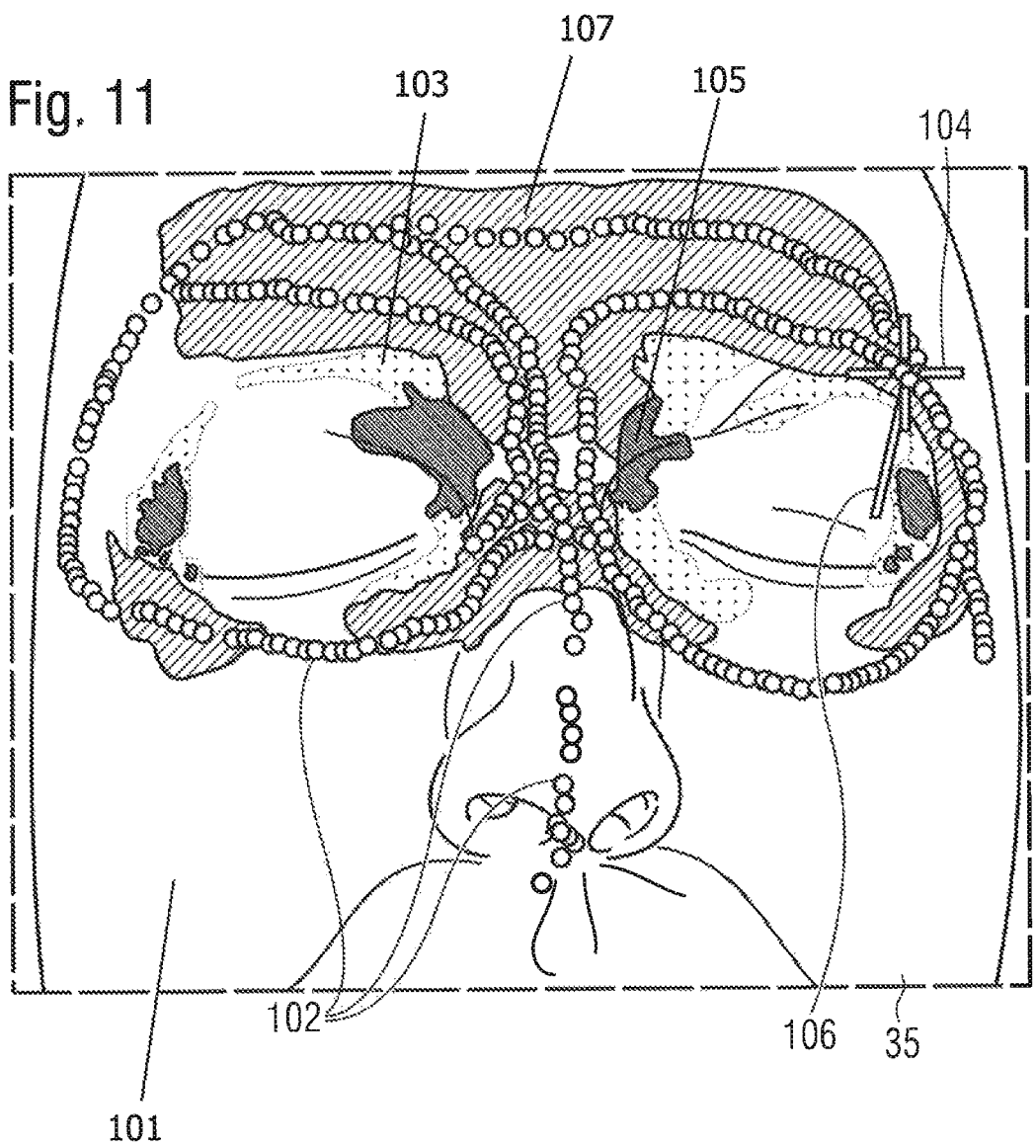

TECHNIQUE FOR GUIDING ACQUISITION OF ONE OR MORE REGISTRATION POINTS ON A PATIENT'S BODY

PRIORITY CLAIM

This application claims priority under 35 U.S.C. § 119 to European Patent Application No. 20198095.0, filed Sep. 24, 2020, the entire contents of which are hereby incorporated by reference.

TECHNICAL FIELD

The present disclosure generally relates to a computer-implemented method, a data processing apparatus and a computer program product, each for guiding a surgeon to acquire one or more registration points on a body of a patient.

BACKGROUND

In surgical navigation, a user such as a surgeon may be provided with information about a relative pose (i.e., at least one of position and orientation) between a surgical instrument (e.g., a chisel, a drill or a probe) and a patient's body. Usually, such information is provided by displaying a visualization of the surgical instrument relative to a medical image of the patient's body, for example an x-ray image, a computer tomography (CT) image or a magnetic resonance (MR) image. This is particularly useful in case of minimally invasive surgeries, where critical anatomical structures such as nerves or arteries may not be visible for the surgeon or a region of interest to be reached with the surgical instrument may be hidden underneath body tissue of the patient.

In the field of surgical navigation, commonly known localization techniques are used in order to determine a current pose of the patient's body and a current pose of the surgical instrument. These localization techniques for example use an optical tracking system comprising a camera for tracking poses of optical trackers attached to the patient's body, and optical trackers attached to the surgical instrument. Alternative localization techniques using electromagnetic, ultrasonic, or other tracking systems have also been described.

It is known how a relative pose between the tracked surgical instrument and the tracked body of the patient can be determined based on the tracked poses of the optical trackers. In order to determine the visualization of the surgical instrument relative to the medical image of the patient's body, it is required to determine a relative pose between the medical image of the patient's body and the tracked patient's body. The relative pose between the medical image and the patient's body can be described by a so-called registration that is usable to transform a pose from a coordinate system of the tracking system into a coordinate system of the medical image and vice versa.

A point-based approach for determining such a registration is commonly used in the field. This approach involves acquiring registration points on the patient's body using a tracked registration probe, and matching positions of these registration points (e.g., described in the coordinate system of the tracking system) to the patient's body as described by the medical image (e.g., to the body described in the coordinate system of the medical image).

An accuracy of a registration determined using this point-based approach significantly depends on where the registration points are acquired on the patient's body. An inaccurate registration between the medical image and the patient's body in turn results in an unrealistic visualization of the surgical instrument relative to the medical image of the patient's body. In certain scenarios, surgeons have to rely heavily on the aforementioned visualization when performing the surgery. In case of an unrealistic visualization, an outcome of the surgery may be negatively affected. It follows that the surgery's outcome depends on where the registration points are acquired on the patient's body. For that reason, surgeons may be insecure about where on the patient's body registration points should be acquired in order to ensure a realistic visualization and improve clinical results.

SUMMARY

There is a need for a technique that guides a surgeon to acquire one or more registration points on a body of a patient.

According to a first aspect, a computer-implemented method for guiding a surgeon to acquire one or more registration points on a body of a patient is provided. The method comprises obtaining geometrical information defining relative positions between a non-patient-specific virtual mask and a plurality of anchor points, each of the anchor points being associated with a non-patient-specific anatomical landmark. The method further comprises obtaining, for each of the anchor points, a position of the associated anatomical landmark in image data of the patient and matching the virtual mask to the image data (e.g., by assigning, to each of the anchor points, the position of the associated anatomical landmark in the image data). The method further comprises obtaining a plurality of image surface points defining a skin surface in the image data. The method comprises determining, based on the matched virtual mask, for at least one of the plurality of image surface points, a priority value indicative of a priority for acquiring a registration point at a position, relative to the body, that corresponds to a position of the at least one image surface point relative to the skin surface defined in the image data. The registration point may (e.g., be configured to) be usable for a registration between the skin surface defined in the image data and the body of the patient based on the at least one image surface point and the registration point. The method of the first aspect also comprises triggering display of a visualization of the priority value of the at least one surface point, or of a visualization of information derived from the priority value.

The virtual mask may be formed as a multi-dimensional mesh comprising a plurality of mesh nodes, wherein each of the anchor points has a known position relative to one or more of the plurality of mesh nodes. In one example, each anchor point coincides with one of the plurality of mesh nodes.

The terms "image surface point" and "surface point" are used herein as synonyms. Determining the priority value may comprise, if the at least one surface point lies outside a registration area, assigning a predefined lower priority value to the at least one surface point, and, if the at least one surface point lies inside the registration area, assigning a predefined higher priority value to the at least one surface point, wherein the registration area is an area of the skin surface designated by the matched virtual mask. The registration area is for example defined by a projection of the matched virtual mask onto the skin surface.

The predefined lower priority value may be selectively assigned to the at least one surface point outside the registration area if the at least one surface point is farther from the registration area than a predefined maximal distance.

Determining the priority value in one example comprises, if the at least one surface point lies outside the registration area and closer to the registration area than the predefined maximal distance, assigning an intermediate priority value smaller than the predefined higher priority value and larger than the predefined lower priority value to the at least one surface point.

Determining the priority value may comprise one of using the assigned priority value as the priority value and weighting the assigned priority value with one or more weighting factors to determine the priority value.

The method may further comprise obtaining a bone surface of the patient's body, determining a shortest distance between the at least one surface point and the bone surface, and determining a first weighting factor of the one or more weighting factors based on the determined shortest distance such that, if the shortest distance is larger, so the assigned priority value of the at least one surface point is weighted less than if the shortest distance is smaller.

In one example, the method comprises determining a second weighting factor of the one or more weighting factors based on an elasticity of body tissue underneath a body point lying on the patient's body such that, if the elasticity of the body tissue underneath the body point has a higher elasticity, the assigned priority value of the at least one surface point is weighted less than if the elasticity of the body tissue underneath the body point has a lower elasticity, wherein the body point has a position relative to the body corresponding to a position of the at least one surface point relative to the skin surface.

The method may comprise determining a third weighting factor of the one or more weighting factors based on a second distance between a position of the at least one surface point relative to the skin surface and a determined position of an obtained registration point relative to the skin surface, such that, if the second distance is smaller, the assigned priority value of the at least one surface point is weighted less than if the second distance is larger.

In one variant, the method further comprises determining a fourth weighting factor of the one or more weighting factors based on an angular difference between a first direction and a second direction, such that, if the angular difference is smaller, the assigned priority value of the at least one surface point is weighted less than if the angular difference is a larger, wherein the first direction is defined by a shape of the skin surface at a position of the at least one surface point relative to the skin surface, and the second direction is defined by a shape of the skin surface at a determined position of an obtained registration point relative to the skin surface.

The third weighting factor and the fourth weighting factor may be determined for each of a plurality of determined positions of obtained registration points, a product of the third weighting factor and the fourth weighting factor may be calculated for each of the plurality of determined positions of the obtained registration points, and the assigned priority value may be weighted with only the largest one of the calculated products.

For example, the method further comprises determining a fifth weighting factor of the one or more weighting factors based on a first direction and a plurality of second directions, such that, if more of a plurality of angular differences between the first direction and each of the plurality of second directions are within a predefined angular range, the assigned priority value of the at least one surface point is weighted less than if fewer of the plurality of angular differences are within the predefined angular range, wherein the first direction is defined by a shape of the skin surface at a position of the at least one surface point relative to the skin surface, and wherein each second direction is defined by a shape of the skin surface at a determined position of one of a plurality of obtained registration points relative to the skin surface.

The fifth weighting factor may further be determined based on a third distance between the at least one surface point and one of the plurality of obtained registration points having a second direction most similar to the first direction among the plurality of second directions, such that, if the third distance is shorter, the assigned priority value of the at least one surface point is weighted less than if the third distance is larger.

The second direction most similar to the first direction may have, among angular differences between the first direction and each of the plurality of second directions, the smallest angular difference.

According to a second aspect, a data processing apparatus for guiding a surgeon to acquire one or more registration points on a body of a patient is provided. The apparatus comprises a processor configured to: obtain geometrical information defining relative positions between a non-patient-specific virtual mask and a plurality of anchor points, each of the anchor points being associated with a non-patient-specific anatomical landmark; obtain, for each of the anchor points, a position of the associated anatomical landmark in image data of the patient; match the virtual mask to the image data (e.g., by assigning, to each of the anchor points, the position of the associated anatomical landmark in the image data); obtain a plurality of image surface points defining a skin surface in the image data; determine, based on the matched virtual mask, for at least one of the plurality of image surface points, a priority value indicative of a priority for acquiring a registration point at a position, relative to the body, that corresponds to a position of the at least one image surface point relative to the skin surface defined in the image data, wherein, optionally, the registration point is usable for a registration between the skin surface defined in the image data and the body of the patient based on the at least one image surface point and the registration point; and trigger display of a visualization of the priority value of the at least one surface point, or of a visualization of information derived from the priority value. The processor comprised in the data processing apparatus may be configured to perform the method of the first aspect.

According to a third aspect, a surgical navigation system is provided. The surgical navigation system comprises the data processing apparatus of the second aspect, a display for displaying the visualization and a tracking system configured to track a registration probe relative to the patient's body to obtain a position of a registration point relative to the body surface.

According to a fourth aspect, a computer program product is provided. The computer program product comprises instructions which, when the program is executed by a processor such as the processor of the data processing apparatus of the second aspect, cause the processor to: obtain geometrical information defining relative positions between a non-patient-specific virtual mask and a plurality of anchor points, each of the anchor points being associated with a non-patient-specific anatomical landmark; obtain, for each of the anchor points, a position of the associated anatomical landmark in image data of the patient; match the virtual mask to the image data (e.g., by assigning, to each of the anchor points, the position of the associated anatomical landmark in the image data); obtain a plurality of image surface points defining a skin surface in the image data; determine, based on the matched virtual mask, for at least one of the plurality of image surface points, a priority value indicative of a priority for acquiring a registration point at a position, relative to the body, that corresponds to a position of the at least one image surface point relative to the skin surface defined in the image data, wherein, optionally, the registration point is usable for a registration between the skin surface defined in the image data and the body of the patient based on the at least one image surface point and the registration point; and trigger display of a visualization of the priority value of the at least one surface point, or of a visualization of information derived from the priority value. The computer program product may comprise instructions which, when the program is executed by a processor, cause the processor to perform the method of the first aspect.

According to a fifth aspect, a computer program is provided comprising instructions which, when the program is executed by a processor, cause the processor to perform the method of the first aspect.

According to a sixth aspect, a carrier medium carrying the computer program of the fifth aspect is provided. The carrier medium may be a (e.g., non-transitory) computer storage medium storing the computer program, a data stream carrying (e.g., information representing) the computer program or a signal wave carrying (e.g., information representing) the computer program.

BRIEF DESCRIPTION OF THE DRAWINGS

Further details, advantages and aspects of the present disclosure will become apparent from the following embodiments taken in conjunction with the drawings, wherein:

FIG. 7 shows two exemplary illustrations of non-patient-specific virtual masks in accordance with the present disclosure;

FIG. 11 shows an exemplary illustration of a visualization of priority values of different surface points in accordance with the present disclosure.

DETAILED DESCRIPTION

Figure 1:
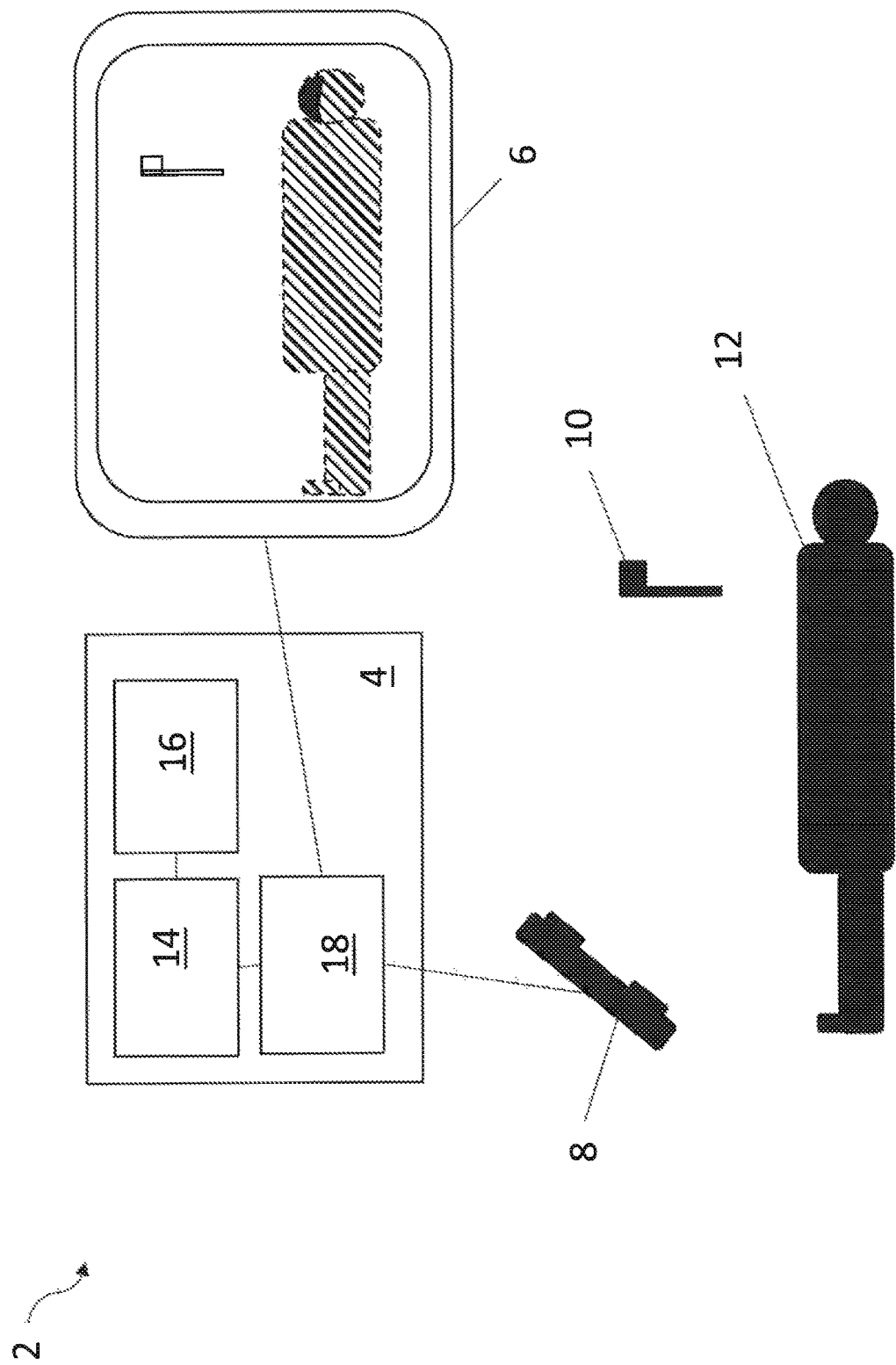
FIG. 1 shows a first exemplary embodiment of a surgical navigation system in accordance with the present disclosure.

In the following description, exemplary embodiments of a surgical navigation system and a surgical navigation method will be explained with reference to the drawings. The same reference numerals denote the same or similar structural features, method steps or determination results.

FIG. 1 shows a first exemplary embodiment of a surgical navigation system 2 in accordance with the present disclosure. The surgical navigation system 2 comprises a data processing apparatus 4, a display 6 and a tracking system 8.

The tracking system 8 may be an optical tracking system and comprise a localizer such as a (e.g., stereoscopic) camera, may be an electromagnetic tracking system comprising an electromagnetic field generator, or may be an ultrasonic tracking system comprising an ultrasonic sound generator. A registration probe 10 may be attached to at least one tracker (not shown) detectable by the tracking system 8. For example, the tracker is an optical tracker detectable by a camera, an electromagnetic sensor configured to detect an electromagnetic field provided by the electromagnetic field generator, or an ultrasonic sensor configured to detect ultrasonic sound signals provided by the ultrasonic sound generator. Similarly, a patient's body 12 may be attached to at least one optical marker, an electromagnetic sensor or an ultrasonic sensor. The aforementioned sensors may be at least one of connected to and part of the tracking system 8.

The tracking system 8 may be configured to determine a pose (i.e., at least one of position and orientation) of the patient's body 12 by tracking the tracker attached thereto. Similarly, the tracking system 8 may be configured to determine a pose of the registration probe 10 by tracking the tracker attached thereto. The tracking system 8, or the apparatus 4 using data obtained from the tracking system 8, may be configured to determine the pose of the patient's body 12 and the registration probe 10 in a "real-world" coordinate system, for example a coordinate system of the tracking system 8, the camera, the electromagnetic field generator or the ultrasonic sound generator. By determining the poses of the patient's body 12 and the registration probe 10, the tracking system 8 or the apparatus 4 using data obtained from the tracking system 8, may be configured to obtain a position of a registration point defined by the registration probe 10 relative to the patient's body 12 in the "real-world" coordinate system.

The data processing apparatus 4 comprises a processor 14, a memory 16 and an (e.g., input/output or transceiver) interface 18. The processor 14 is coupled to the memory 16 and the interface 18. The interface is coupled to the tracking system 8 and the display 6. Note that the interface 18 may comprise two separate interface units (not shown), a first interface unit being connected only to the display unit 6 and a second interface unit being connected only to the tracking system 8. The processor 14 is configured to perform the method as described herein. For example, the memory 16 stores instructions that, when executed by the processor 14, cause the processor 14 to perform the method as described herein.

Figure 2:
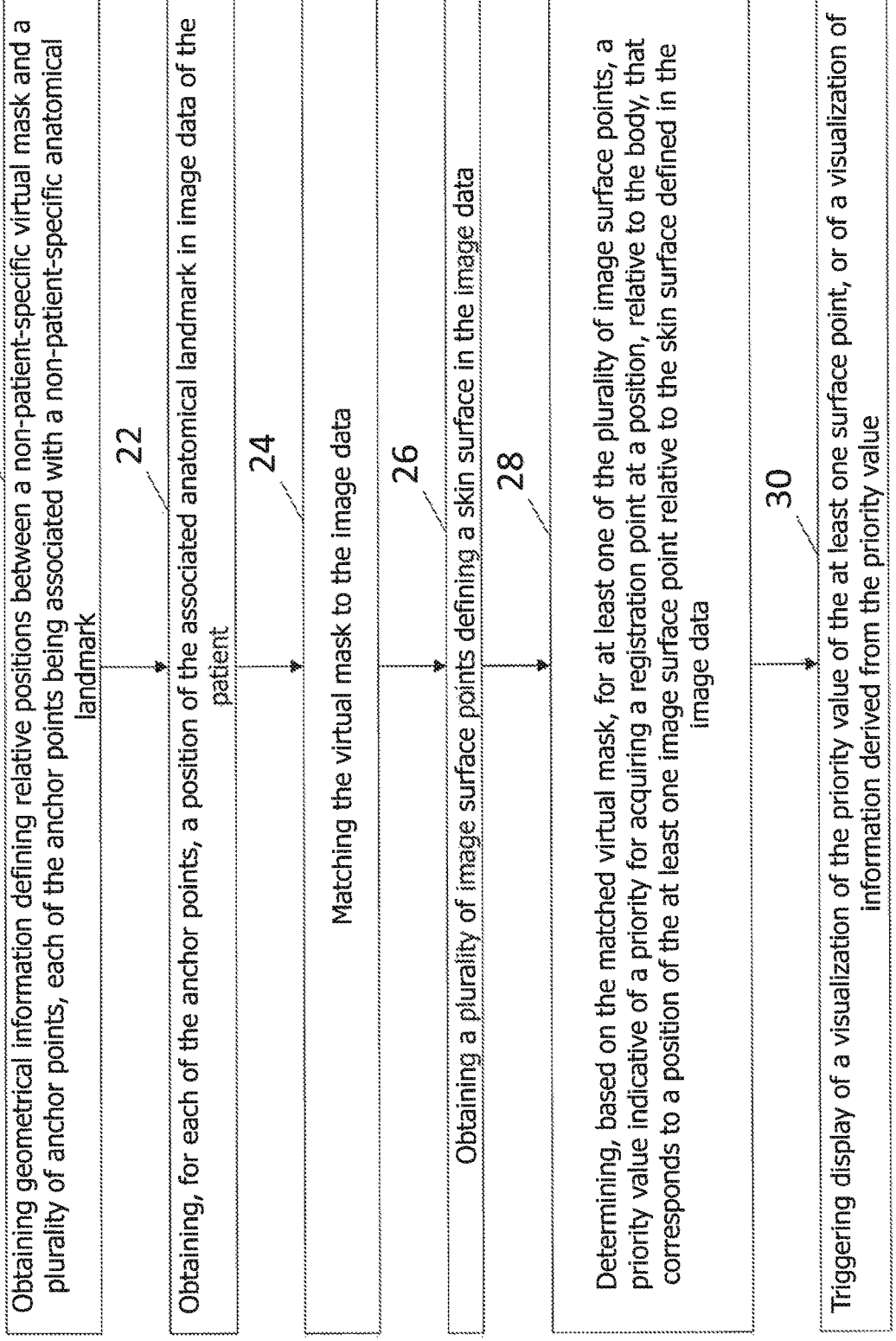
FIG. 2 shows a first exemplary embodiment of a method in accordance with the present disclosure.

FIG. 2 shows a first exemplary embodiment of a method in accordance with the present disclosure. This method may be performed by the processor 14.

In step 20, geometrical information is obtained (e.g., in the form of computer-readable geometrical information data), defining relative positions between a non-patient-specific virtual mask and a plurality of anchor points. For instance, the non-patient specific mask may be described by coordinates (e.g., in a "virtual-world" coordinate system different from the "real-world" coordinate system, for example in a coordinate system of the non-patient-specific virtual mask) of a plurality of mask points defining the virtual mask. The geometrical information may then define, for each of the plurality of anchor points, a relative position to the coordinates of one or more of the plurality of mask points. In one variant, each anchor point coincides with one of the plurality of mask points. The number of anchor points may be equal to the number of mask points. The geometrical information may be obtained based on input of a user, for example a selection of one of a plurality of virtual masks. Alternatively, the virtual mask may be selected from a plurality of virtual masks based on a property of image data of the patient.

The virtual mask may be formed as a multi-dimensional (e.g., two or three-dimensional) mesh comprising or consisting of a plurality of mesh nodes, wherein each of the anchor points has a known position relative to one or more of the plurality of mesh nodes. In this case, the mesh nodes may correspond to the aforementioned mask points. The virtual mask may represent or define a virtual topological surface or a three-dimensional geometrical body.

The virtual mask is non-patient-specific as it is suitable for a plurality of different patients. Each of the anchor points is associated with (e.g., at least or exactly one) non-patient-specific anatomical landmark. The non-patient-specific anatomical landmarks may be points on a body surface of a human body and detectable in image data of a patient's body. The non-patient-specific landmarks may include one or more of a nose tip, a subnasale, a nasion, an endocanthion, an exocanthion and a (e.g., point defining a) symmetry plane.

In step 22, for each of the anchor points, a position of the associated anatomical landmark in the image data of the patient is obtained (e.g., in a coordinate system of the image data). For instance, a first anchor point may be associated with the non-patient-specific landmark of a nose tip, and a position of the nose tip may be obtained in image data of the patient.

The step 22 may comprise determining the position of the associated anatomical landmark based on the image data, for example by identifying a point on the patient's body as described by the image data based on predetermined attributes correlated with the associated anatomical landmark. For example, a certain curvature range of a surface of a body may be correlated with a nose tip, and a corresponding position may then be detected in the image data by analysing the curvature of the surface of the body as described by the image data. The expression "based on" as used herein in one variant means "only based on", and in another variant means "based on at least".

Alternatively, the step 22 may comprise obtaining (e.g., position data describing or defining) a predetermined position as the position of the associated anatomical landmark in the image data. The predetermined position may be pre-set by a surgeon or determined based on the image data in advance.

The image data of the patient may be medical image data of the body 12 of the patient, such as x-ray, computer tomography (CT) or magnetic resonance (MR) image data. The image data of the patient may comprise at least one medical image of the body 12 of the patient, for example at least one of an x-ray image, a CT image and an MR image.

In step 24, the non-patient-specific virtual mask is matched to the image data, for example by assigning, to each of the anchor points, the position of the associated anatomical landmark in the image data. This matching step may comprise at least one of deforming the virtual mask and transforming the virtual mask into a coordinate system of the image data or vice versa. One may say that in step 24, a (e.g., deforming or rigid) registration is determined between the non-patient-specific virtual mask and the image data. For example, each of the anchor points is assigned the position of the associated anatomical landmark in a coordinate system of the image data. Such assignment may lead to a change in relative positions between the anchor points, thereby deforming the non-patient-specific virtual mask by matching it to the image data. While the virtual mask before the matching step is non-patient-specific, the matched mask is patient-specific. This is because the matched mask is modified to comply with the anatomical landmarks in the image data of the patient. The method may then continue with a step 26.

In one exemplary implementation that is not part of the claims of the current application, the non-patient-specific virtual mask is matched to the image data by transforming positions of the anchor points into the coordinate system of the image data, for example using an obtained (e.g., predetermined, rigid or non-rigid) registration between the coordinate system of the virtual mask and the coordinate system of the image data. In this case, the anchor points do not necessarily need to be associated with anatomical landmarks, and the steps 22 to 24 may be avoided. In other words, the method may in this case comprise a step of obtaining geometrical information defining relative positions between a non-patient-specific virtual mask and a plurality of anchor points, a step of obtaining image data of a patient, a step of obtaining a registration between (e.g. the coordinate system of) the image data and (e.g., the coordinate system of) the virtual mask, and a step of matching the virtual mask to the image data using the obtained registration, for example by assigning, to each of the anchor points, positions in the coordinate system of the image data. This exemplary implementation may comprise or continue with step 26.

In step 26, a plurality of image surface points (also referred to as "surface points" herein) defining a skin surface in the image data (e.g., in the image comprised in the image data) are obtained. This step may comprise determining the plurality of image surface points based on the image data or obtaining (e.g., surface data comprising or defining) a plurality of predetermined patient-specific points as the image surface points. The image surface points are patient-specific, as they define a skin surface in the image data of the patient's body. The image surface points may be defined in the coordinate system of the image data. The skin surface may be identified in the image data using one or more threshold values, for example a minimum Hounsfield value of pixels in a two-dimensional medical image or of voxels in a three-dimensional medical image. Alternatively or additionally, one or more computer vision algorithms may be used to identify the skin surface in the image data.

In step 28, based on the matched virtual mask, for at least one of the plurality of image surface points, a priority value is determined. The priority value is indicative of a priority for acquiring a (e.g., corresponding) registration point at a position, relative to the body 12 (e.g., in the "real-world" coordinate system such as the coordinate system of the tracking system 8), that corresponds to a position of the at least one image surface point relative to the skin surface defined in the image data (e.g., in the "virtual-world" coordinate system such as the coordinate system of the image data).

For example, the priority is indicative of a high priority for acquiring a corresponding registration point at a position of the nose tip of the patient's body 12 using the registration probe 10, which corresponds to a position of the nose tip in the image data. As another example, the priority may be indicative of a low priority for acquiring a corresponding registration point at a position on the lower right cheek of the patient's body, which corresponds to a position on the lower right cheek of the body as described by the image data. The corresponding registration point may be acquired using the registration probe 10.

The registration point may be usable for (e.g., determining) a registration between the skin surface defined in the image data and the body of the patient based on the at least one image surface point and the registration point. The method may comprise using the registration point for (e.g., determining) a registration between the skin surface defined in the image data and the body 12 of the patient based on the at least one image surface point and the registration point. A higher priority value may indicate a higher suitability of the registration point for the registration, whereas a lower priority value may indicate a lower suitability.

For example, a registration between the skin surface defined in the image data and a surface of the body 12 may be determined by matching the position of the at least one image surface point (e.g., described in the coordinate system of the image data) to the position of the corresponding registration point (e.g., described in the coordinate system of the tracking system 8) once it has been acquired, using a so-called point-to-point matching. Alternatively, the position of the corresponding registration point may be matched to the skin surface using a so-called point-to-surface matching. In other words, a transformation from the "real-word" coordinate system to the "virtual-world" coordinate system (e.g., the coordinate system of the image data) or vice versa may be determined using the corresponding registration point and the image data (e.g., by applying a point-to-point matching or a point-to-surface matching algorithm).

Alternatively or additionally, an existing registration between the two aforementioned coordinate systems may be updated, enriched or improved by matching the position of the at least one image surface point or the skin surface to the position of the acquired corresponding registration point. For example, the existing registration may have been determined using a low number of acquired corresponding registration so points. Then, using an additional corresponding registration point, the existing registration may be determined once again using not only the low number of acquired corresponding registration points, but also the additional corresponding registration point.

Different acquired registration points may be given different weights when using the acquired registration points for (e.g., determining, updating or improving) the registration. The priority value of the at least one image surface point may be at least one of correlated with, based on, proportional and equal to the weight of the acquired corresponding registration point to be used for the registration.

In step 30, display of a visualization of the priority value of the at least one surface point, or of a visualization of information derived from the priority value is triggered. Visualizations of priority values of a multitude of surface points may be triggered in case step 28 is performed for the multitude of surface points. The processor 14 may send a trigger signal to the display 6 for triggering display of the visualization(s).

Note that the sequence of steps 22 and 24 may be reversed. Step 26 may be performed before one or more of steps 20, 22 and 24.

In short, the method described herein provides a user such as a surgeon with a visualization of a priority value of an image surface point that has a corresponding registration point on the patient's body 12. For example, a virtual representation (e.g., an image) of the patient's body 12 and an indication of the position of the at least one image surface point is triggered to be displayed on the display 6. Additionally, the visualization of (e.g., the information derived from) the priority value of the at least one image surface point may be triggered to be displayed, for example as a number, a color, a text, a symbol, a blinking pattern or else. The steps 28 and 30 may be performed for a plurality of image surface points. In this case, indications of the plurality of surface points may be triggered to be displayed, as well as visualizations of the priority values thereof. Exemplary realizations of such a display will be described below with reference to FIGS. 8, 10 and 11. Based on the triggered display, the user may decide whether to acquire the corresponding registration point on the patient's body 12 or not. This helps the user in choosing suitable registration points for acquisition. If the acquired registration points are used for determining or improving a registration between the "virtual-world" coordinate system and the "real-world" coordinate system, an accuracy of the registration may be improved.

Figure 3:
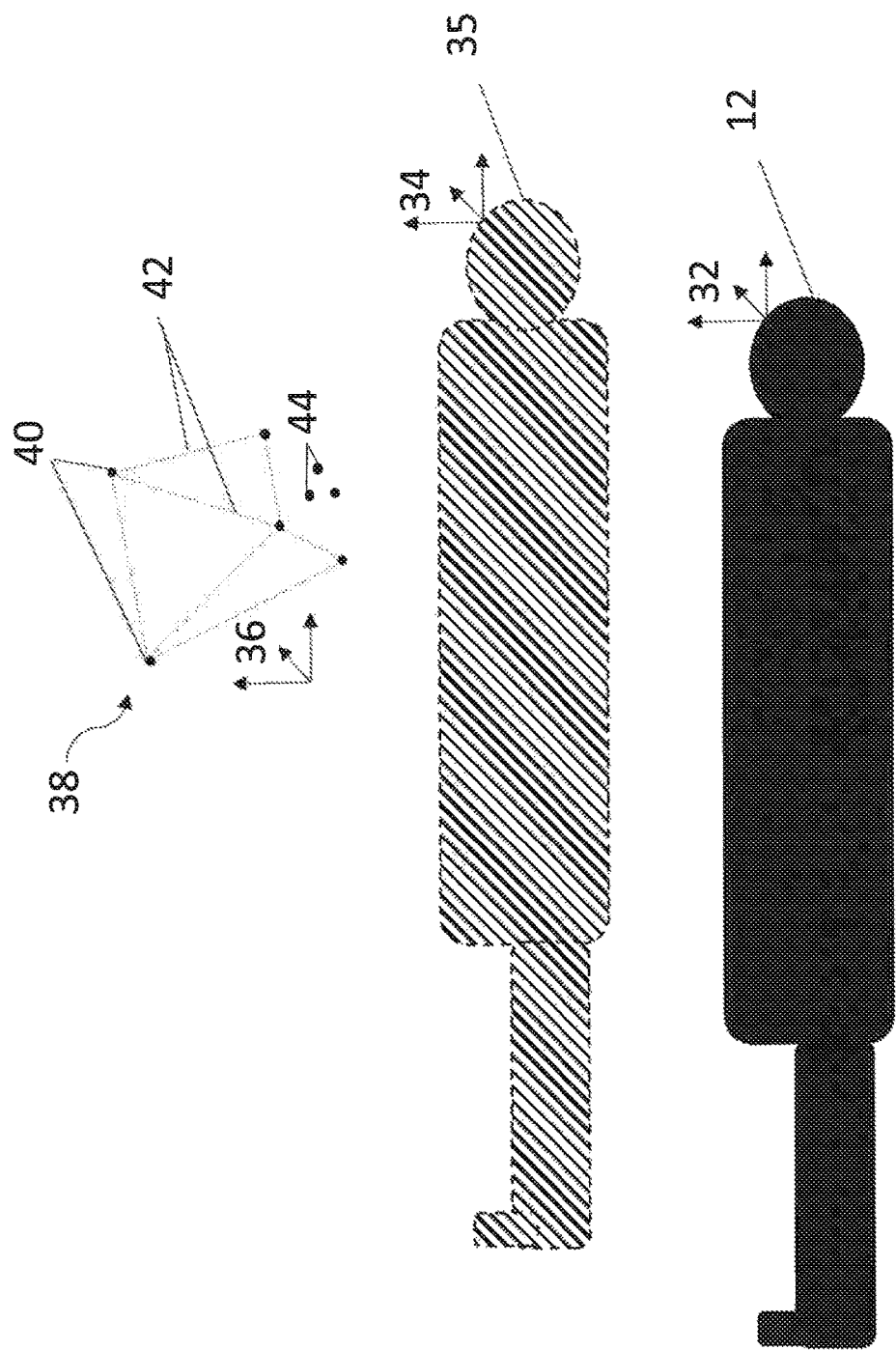
FIG. 3 shows an exemplary illustration of a patient's body and a virtual mask in accordance with the present disclosure.

FIG. 3 shows an exemplary illustration of the patient's body 12 and an example of the non-patient-specific virtual mask 38 with the mesh nodes 40 and mesh lines 42 connecting the mesh nodes 40. The patient's body 12 has a known pose in the coordinate system 32 (e.g., the "real-world" coordinate system or the coordinate system of the tracking system 8). The image data that describes the patient's body 12 is associated with or defined in the coordinate system 34 of the image data and in the shown example comprises an image 35 of the patient's body 12. The image 35 has a known pose in the coordinate system 34. The virtual mask 38 is associated with or described in a third (e.g., the "virtual-world") coordinate system 36. Each of the mesh nodes 40 has a known position relative to the anchor points 44 in the third coordinate system 36.

Before matching the non-patient-specific virtual mask 38 to the image 35 (e.g. in step 24), no transformation or positional relationship between the coordinate systems 34 and 36 may be known. Alternatively, a relative pose between the coordinate systems 34 and 36 may already be known. In one example, the coordinate systems 34 and 36 coincide with or are equal to one another.

After matching the non-patient-specific virtual mask 38 to the image 35 by assigning, to each of the anchor points 44, the position of the associated anatomical landmark in the image 35, the position of the mesh nodes 40 and the poses of the mesh lines 42 can be determined in the coordinate system 34.

The matched virtual mask may designate a registration area. For example, the registration area may be defined by a projection of (e.g., a coverage area of) the matched virtual mask onto the skin surface in the image data. In one example, each of a plurality of points of the matched virtual mask (e.g., each of the mesh nodes 40 and/or a plurality of points on the mesh lines 42) are projected onto closest points on the skin surface in the image data. That is, the projection direction of each of the plurality of points of the matched virtual mask may be normal to the skin surface. The registration area may have an outline defined by an outer border of the matched mask projected onto the skin surface. As will be described in the following, such a registration area can be used to determine the priority value of the at least one image surface point.

Figure 4:
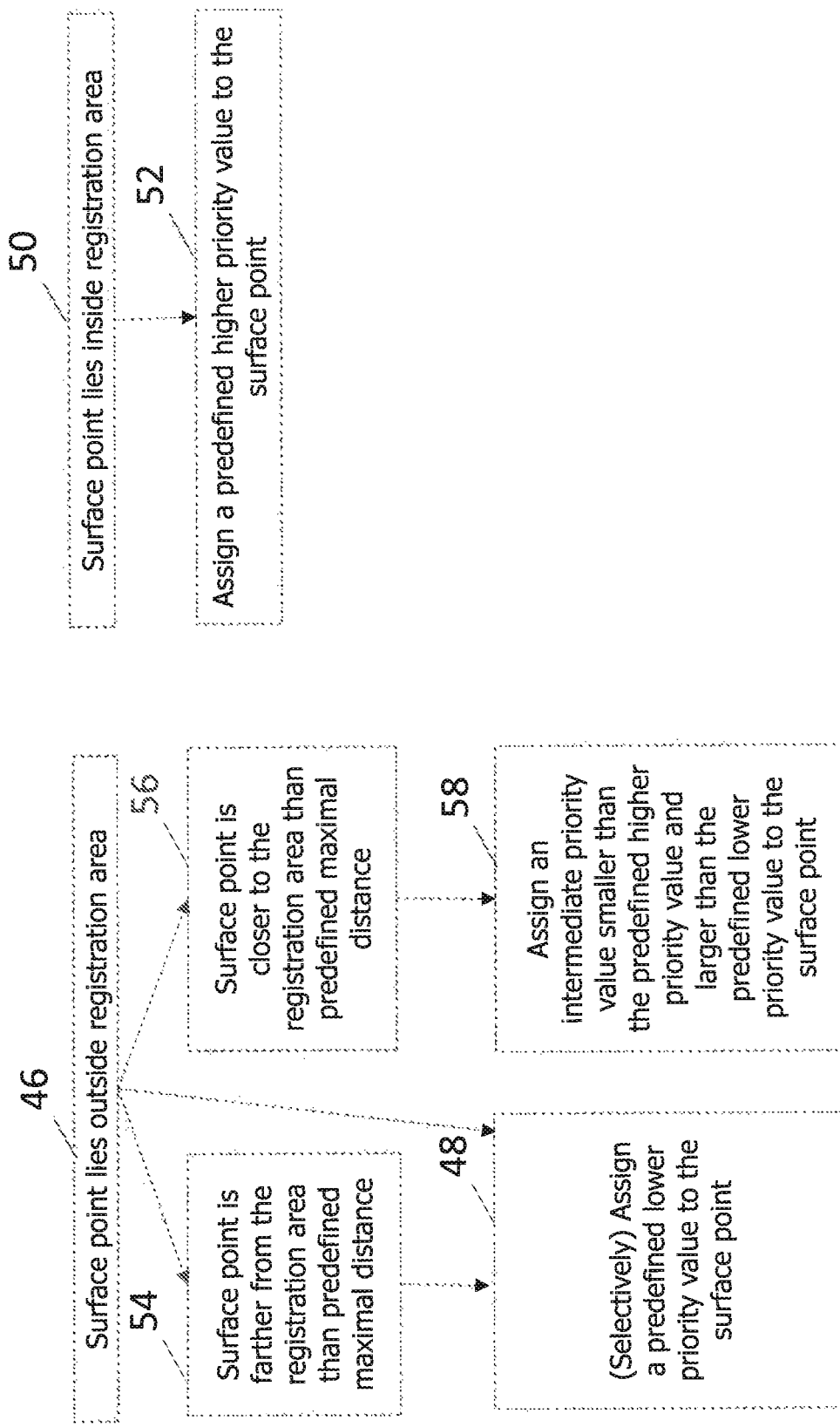
FIG. 4 shows exemplary steps that may be part of a method in accordance with the present disclosure.

FIG. 4 shows exemplary steps that may be part of the method as described herein. For example, the method shown in FIG. 2 comprises one or more of the steps of FIG. 4. The data processing apparatus 4, in particular the processor 14, may be configured to perform one or more of the steps shown in FIG. 4.

It may be determined that the at least one surface point lies outside the registration area (step 46). In this case, the method may proceed with assigning a (e.g., preliminary) predefined lower priority value to the at least one surface point (step 48). On the other hand, if it is determined that the at least one surface point lies inside the registration area (step 48), the method may proceed with assigning a (e.g., preliminary) predefined higher priority value to the at least one surface point (step 50).

It may be determined that the at least one surface point lies outside the registration area and farther from the registration area than a predefined maximal distance (step 54). In this case, the method may proceed with selectively assigning the predefined (e.g., preliminary) lower priority value to the at least one surface point (step 54). On the other hand, it may be determined that the at least one surface point lies outside the registration area and closer to the registration area than the predefined maximal distance (step 56). In this case, the method may proceed with assigning an (e.g., preliminary) intermediate priority value smaller than the predefined higher priority value and larger than the predefined lower priority value to the at least one surface point. Steps 46 and 54 may be combined in a single step. Similarly, steps 46 and 56 may be combined in another single step. Others of the shown steps may also be combined if deemed appropriate.

The step 28 of determining the priority value may comprise using the assigned (e.g., preliminary) priority value as the (e.g., final) priority value.

Alternatively, the step 28 may comprise weighting the assigned (e.g., preliminary) priority value with one or more weighting factors to determine the (e.g., final) priority value. In the following, examples of such weighting factors will be given.

A first weighting factor of the one or more weighting factors may be determined. The first weighting factor yields a higher priority value if a distance between the skin surface and a bone surface is smaller. This is because, generally speaking, acquired registration points should have a fixed position relative to the patient's body. Most surgical procedures tend to happen inside the body. Thus, the acquired registration points should have a fixed position relative to inner parts of the body, in particular relative to bones. On the other hand, when acquiring registration points on a surface of a patient's body, these points may not have fixed positions relative to the bones because the body tissue underneath the body surface may move relative to the bones. Such movement is lower for smaller tissue thicknesses between the bone and the body surface.

Therefore, the method may comprise obtaining the bone surface of the patient's body (e.g., in the image data). The bone surface may be predetermined or be determined based on the image data, for example using a pattern recognition algorithm or one or more intensity thresholds (e.g., Hounsfield value thresholds). The method may comprise determining a shortest distance between the at least one surface point and the bone surface (e.g., in the coordinate system of the image data). The first weighting factor may then be determined based on the determined shortest distance such that, if the shortest distance is larger, the assigned priority value of the at least one surface point is weighted less than if the shortest distance is smaller.

In one example, the first weighting factor is determined according to the following formula 1.

$$W_1 = \max\left\{1 - \frac{d}{d_{max}}, 0\right\} \quad \text{(Formula 1)}$$

In this formula, Wi denotes the first weighting factor, d denotes the determined shortest distance between the at least one surface point and the bone surface and $d_{max}$ is a numerical value. For example, $d_{max}$ corresponds to 7.5 mm. According to this formula, the first weighting factor has a value between 0 and 1.

In another example, the first weighting factor is determined according to the following formula 2.

$$W_1 = \max\left\{1 - \left(\frac{\max\{d - d_{Opt}, 0\}}{d_{max} - d_{Opt}}\right)^2, 0\right\} \quad \text{(Formula 2)}$$

In this formula, Wi denotes the first weighting factor, d denotes the determined shortest distance between the at least one surface point and the bone surface and $d_{max}$ and $d_{Opt}$ are numerical values. For example, $d_{max}$ corresponds to 7.5 mm and $d_{Opt}$ corresponds to 5 mm. According to this formula, the first weighting factor has a value between 0 and 1.

A second weighting factor of the one or more weighting factors may be determined. The second weighting factor may yield a higher priority value if a body tissue underneath the corresponding registration point has a low elasticity. As in the case of the first weighting factor, lower elasticity of underlying body tissue improves a positional rigidness or continuity between the position of the registration point and a center of the body.

The method may therefore comprise determining the second weighting factor based on an elasticity of body tissue underneath a body point lying on (e.g., the surface of) the patient's body such that, if the elasticity of the body tissue underneath the body point has a higher elasticity, the assigned priority value of the at least one surface point is weighted less than if the elasticity of the body tissue underneath the body point has a lower elasticity, wherein the body point has a position relative to the body surface (e.g., in the "real-world" coordinate system) corresponding to a position of the at least one surface point relative to the skin surface (e.g., in the coordinate system of the image data). The body point may be equal to the corresponding registration point of the at least one image surface point.

A third weighting factor of the one or more weighting factors may be determined. The third weighting factor may yield a lower priority if registration points have already been obtained at positions close to the corresponding registration point of the at least one surface point. This is because for a registration to be accurate, the acquired registration points should be spaced from one another to avoid ambiguities and allow for an improved point matching result.

The method may therefore comprise determining the third weighting factor based on a second distance between a position of the at least one surface point relative to the skin surface and a determined position of an obtained registration point relative to the skin surface, such that, if the second distance is smaller, the assigned priority value of the at least one surface point is weighted less than if the second distance is larger.

The position of the obtained registration point relative to the skin surface may be determined by obtaining or determining a position of the obtained registration point in the "real-world" coordinate system and transforming this position into the coordinate system of the image data using a known (e.g., predetermined or "rough") registration. If the obtained and transformed position of the obtained registration point does not lie on the skin surface, it may be projected onto the skin surface (e.g., onto a closest point on the skin surface). Note that the "obtained" registration point may correspond to an "acquired" registration point according to the present disclosure.

A fourth weighting factor of the one or more weighting factors may be determined. The fourth weighting factor may yield a lower priority value of the at least one surface point if a shape of a surface of the patient body 12 at the corresponding registration point is closely similar to a shape of the patient body's 12 surface at a position of an already obtained registration point. This is because for a registration to be accurate, the acquired registration points used for determining or updating the registration should be placed on body portions having different inclinations to avoid ambiguities and improve the point matching results.

The method may therefore comprise determining the fourth weighting factor based on an angular difference between a first direction and a second direction, such that, if the angular difference is smaller, the assigned priority value of the at least one surface point is weighted less than if the angular difference is a larger, wherein the first direction is defined by a shape (e.g., a gradient, curvature or normal) of the skin surface at a position of the at least one surface point relative to the skin surface (e.g., in the coordinate system of the image data), and the second direction is defined by a shape (e.g., a gradient, curvature or normal) of the skin surface at a determined (e.g., obtained and transformed) position of an obtained registration point relative to the skin surface. A normal of the skin surface at the obtained and transformed (and possibly projected) position of the obtained registration point may be compared with a normal of the skin surface at the position of the at least one image surface point. The smaller the angular deviation between the two normals, the smaller may be the fourth weighting factor.

In one example, the third weighting factor and the fourth weighting factor are determined for each of a plurality of determined positions of obtained registration points, a product of the third weighting factor and the fourth weighting factor is calculated for each of the plurality of determined (e.g., obtained, transformed and possibly projected) positions of the obtained registration points, and the assigned priority value is weighted with only the largest one of the calculated products.

For example, the products are determined according to formula 3 as follows.

$$P=\text{dist}(S,R_{obt})*\sin(\text{angle}(n_S,n_R))$$ (Formula 3)

In this formula, P denotes the product between the third weighting factor and the fourth weighting factor. The third weighting factor is represented by the multiplicand and the fourth weighting factor by the multiplicator. As can be seen, the third weighting factor corresponds to the distance between the at least one surface point S and the determined position of the obtained registration point $R_{obt}$ in the coordinate system of the image data. The fourth weighting factor corresponds to the sine value of the angle between the normal $n_S$ of the skin surface at the position of the at least one surface point and the normal $n_R$ of the skin surface in the determined position of the obtained registration point in the coordinate system of the image data. It is noted that the third weighting factor, the fourth weighting factor or the products P may be normalized using one or more normalization functions such that the third weighting factor, the fourth weighting factor and/or the products P have a value between 0 and 1.

A fifth weighting factor of the one or more weighting factors may be determined. The fifth weighting factor may yield a lower priority if the direction defined by the shape of the skin surface at the position of the at least one surface point falls within a predefined range of directions that is already covered by several directions defined by the shape of the skin surface at determined positions of obtained registration points. This approach goes into the same direction as the fourth weighting factor. Likewise, for a registration to be accurate, the acquired registration points used for determining the registration should be placed on body portions having different inclinations to avoid ambiguities and improve the point matching results.

The method may therefore comprise determining the fifth weighting factor based on a first direction and a plurality of second directions, such that, if more of a plurality of angular differences between the first direction and each of the plurality of second directions are within a predefined angular range, the assigned priority value of the at least one surface point is weighted less than if fewer of the plurality of angular differences are within the predefined angular range, wherein the first direction is defined by a shape of the skin surface at a position of the at least one surface point relative to the skin surface (e.g., in the coordinate system of the image data), and wherein each second direction is defined by a shape of the skin surface at a determined position of one of a plurality of obtained registration points relative to the skin surface (e.g., in the coordinate system of the image data). The positions of the obtained registration points can be determined in the coordinate system of the image data as noted above (e.g., by obtaining, transforming and possibly projecting the positions of the registration points).

According to the present disclosure, a direction defined by a shape of the skin surface at a given position may correspond to an average normal of a predetermined area of the skin surface surrounding the given position (e.g., the position of the at least one surface point or the determined position of the obtained registration point). The predetermined area may consist of surface points having a distance to the given position that is below a predetermined distance threshold, for example below 2 mm. The average normal may be determined as an arithmetic average of three-dimensional vectors describing normals of the skin surface. For instance, the skin surface is defined by a mesh comprising the (image) surface points as mesh nodes, wherein mesh planes are defined having the mesh nodes as corners. A direction at the position of a mesh node of the skin surface may then be determined by weighting normals of mesh planes of which the mesh node forms a corner. The normal of the mesh planes may be weighted with area sizes of the mesh planes of which the mesh node forms a corner and an arithmetic average of the weighted normal may be set as the direction. A normal of a surface point not corresponding to a mesh point may be determined by interpolation (e.g., using Phong shading) of the normals determined for the mesh nodes.

Again, registration points on surface portions having the same inclination should at least be distant from one another to improve a subsequent point matching, reduce ambiguities and improve registration accuracy when being used for the registration.

Therefore, the fifth weighting factor may be further determined based on a third distance between the at least one surface point and one of the plurality of obtained registration points having a second direction most similar to the first direction among the plurality of second directions, such that, if the third distance is shorter, the assigned priority value of the at least one surface point is weighted less than if the third distance is larger. The second direction most similar to the first direction may have, among angular differences between the first direction and each of the plurality of second directions, the smallest angular difference.

Alternatively, the fifth weighting factor may be further determined based on a fourth distance between the at least one surface point and one of the plurality of obtained registration points that is, among all obtained registration points having a second direction falling within the predefined angular range (e.g., having an angular difference of the second direction relative to the first direction that is lower than a given threshold), closest to the at least one surface point, such that, if the fourth distance is shorter, the assigned priority value of the at least one surface point is weighted less than if the fourth distance is larger.

In one example, the first weighting factor is determined according to the following formula 4.

$$W_4 = \frac{D/A}{N/B} \quad \text{(Formula 4)}$$

In this formula, $W_4$ denotes the fourth weighting factor. D denotes the distance dist(S, $R_{obt,close}$) between the at least one surface point S and the position of a closest ($R_{obt,close}$) of the obtained registration points $R_{obt}$ in the coordinate system of the image data, wherein the closest of the obtained registration points optionally has a second direction falling within the predefined angular range. N corresponds to the number of obtained registration points having second directions defining angular differences relative to the first direction that fall within the predefined angular range. A and B correspond to potentially different numerical values. For example, B represents an expected density of second directions of registration points to be used for determining or updating the registration. The parameter B may corresponds to a total number of registration points to be used for the registration, divided by a total angular area to be covered (e.g., 480 (registration points to be used) divided by an angular area of 90°*120° leads to a value of A=480/(90*120)=0.444). An exemplary value of B is 0.02. The parameter A may represent a maximal value for the distance between the at least one surface point and the position of a closest of the obtained registration points $R_{obt}$ in the coordinate system of the image data, wherein the closest of the obtained registration points has a second direction falling within the predefined angular range. An exemplary value of A is 30 mm.

Figure 5:
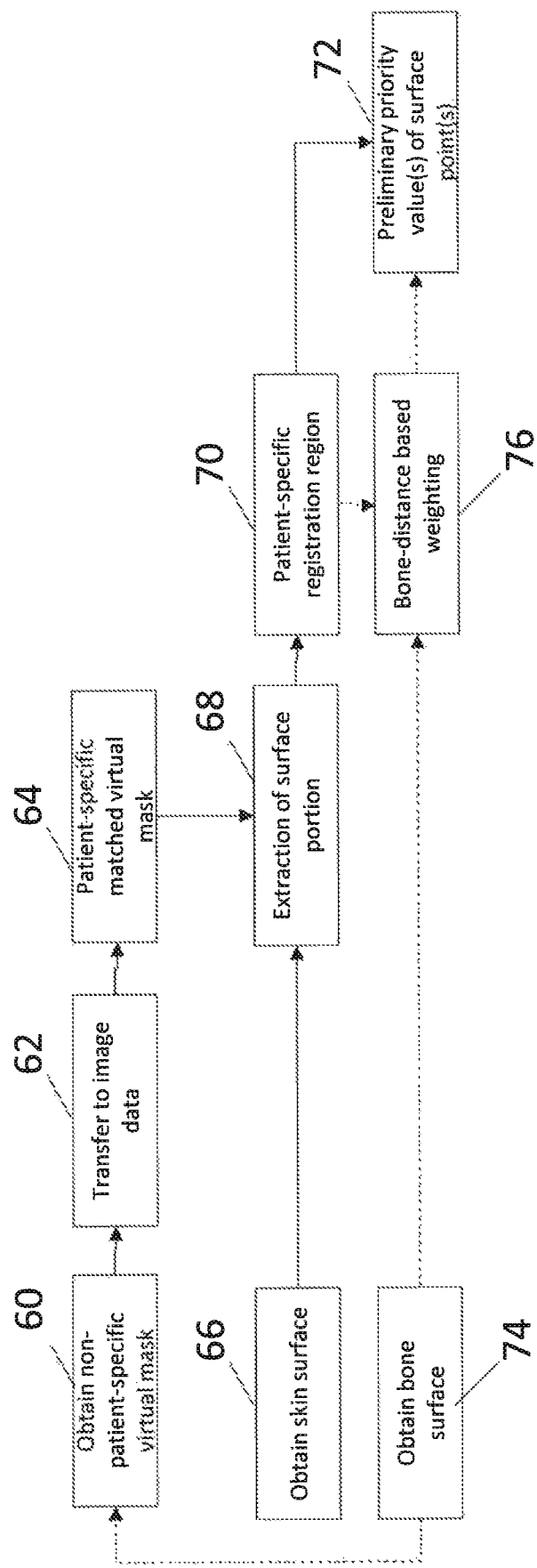
FIG. 5 shows a flowchart illustrating an exemplary sequence of method steps in accordance with the present disclosure.

FIG. 5 shows a schematic flowchart illustrating an exemplary sequence of method steps in accordance with the present disclosure. The method may be performed by the processor 14. The method shown in FIG. 5 may be combined with the method described above.

The method comprises a step 60 of obtaining the non-patient specific virtual mask. In particular, as described above for step 20, geometrical information defining relative positions between the non-patient-specific virtual mask and a plurality of anchor points may be obtained in step 60, each of the anchor points being associated with one of the non-patient-specific anatomical landmarks.

In step 62, the non-patient specific virtual mask is transferred to the image data of the patient. This step may comprise or correspond to the steps 22 and 24 described above. As a result 64 of step 62, the patient-specific matched virtual mask is obtained.

The method further comprises obtaining (e.g., determining) the skin surface in the image data (step 66), the skin surface being defined by the plurality of surface points. In step 68, the patient-specific matched virtual mask is used to extract a portion of the skin surface. For instance, the matched mask is projected onto the skin surface as described above to extract the portion of the skin surface. As a result 70 of the step 68, the patient-specific registration region is obtained.

The registration region may be used to determine, as the result 72, the preliminary priority value(s) of the at least one surface point or of all surface points. For example, the assigned (e.g., lower, higher or intermediate) priority value described above may be used as the preliminary priority value. That is, the preliminary priority value of the at least one surface point may be determined only based on the skin surface, the registration region and the position of the at least one surface point. The preliminary priority value may be determined based on the registration region as described above with reference to FIG. 4.

In an optional step 74, the bone surface in the image data is obtained. The bone surface is used in an optional step 76 to apply a bone-distance based weighting to determine the preliminary priority value. Note that step 76 may correspond to using the first or second weighting factor described above to weight the assigned priority value.

As indicated in FIG. 5, the bone surface may be used for obtaining the non-patient specific virtual mask. That is, the non-patient specific virtual mask may be adjusted or selected from a plurality of non-patient specific virtual masks based on whether the bone surface is at least one of obtained, known or determinable from the image data.

In one example, the method with the result 72 proceeds with step 30. In this case, the preliminary priority value may be used as the priority value. In another example, the preliminary priority value may be used to determine the priority value. Such an example will now be described with reference to FIG. 6.

Figure 6:
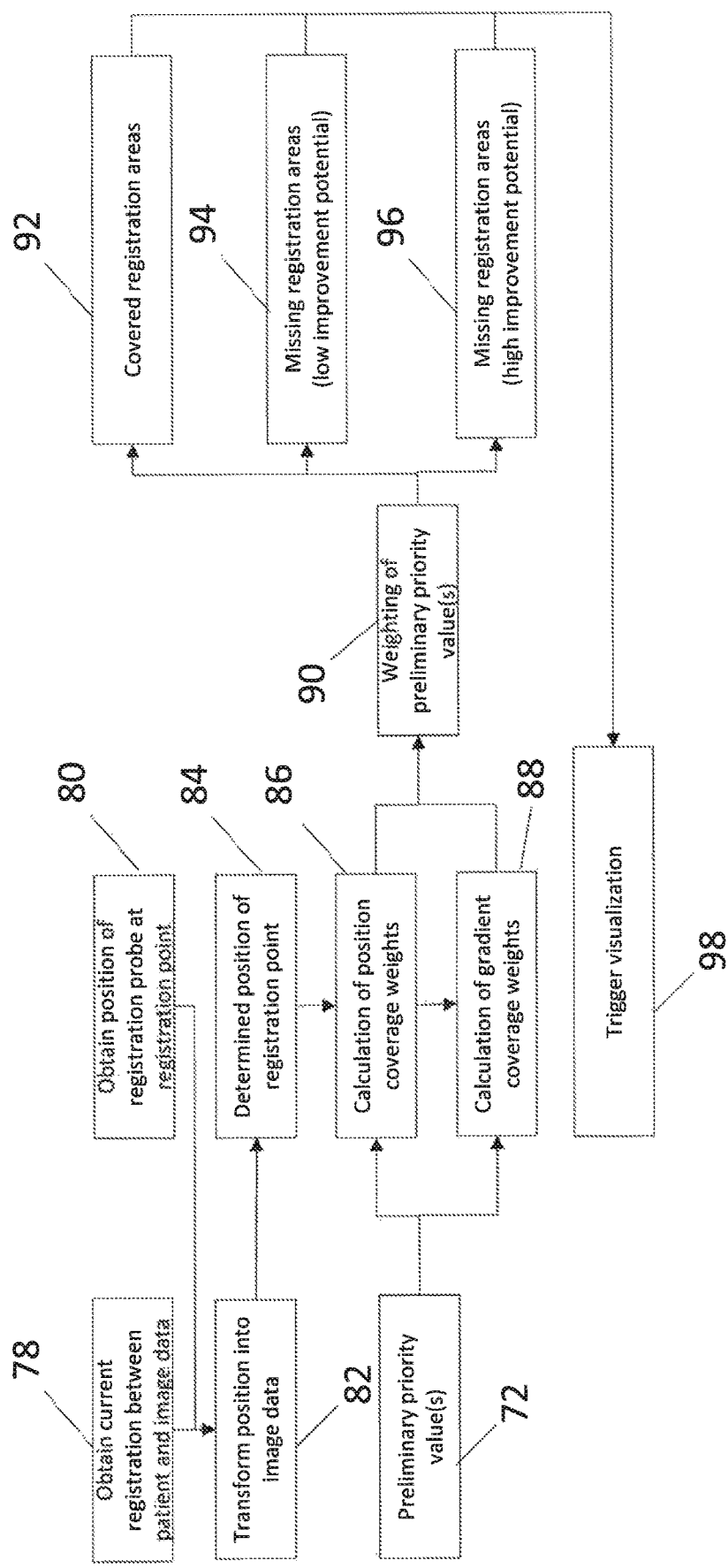
FIG. 6 shows a flowchart illustrating an exemplary sequence of method steps in accordance with the present disclosure.

FIG. 6 shows a schematic flowchart illustrating an exemplary sequence of method steps in accordance with the present disclosure. The method may be performed by the processor 14. As can be seen, the result 72, namely, the preliminary priority values determined in accordance with the method shown in FIG. 5, is used.

In step 78, a current (e.g., determined) registration between the patient's body 12 (e.g., the coordinate system of the tracking system 8) and the image data (e.g., the coordinate system of the image data) is obtained. In step 80, a position of (e.g., a distal tip of) the registration probe 10 (e.g., in the coordinate system of the tracking system 8) at a registration point is obtained. In step 82, the position of the registration point is transformed into the image data. For example, the position of the distal tip of the registration probe 10 as described in the coordinate system of the tracking system 8 is transformed into a position as described in the coordinate system of the image data using the current registration. As a result 84, the step 82 yields the determined so position of the registration point in the coordinate system of the image data. The transformed position of the registration point may optionally be projected onto the skin surface in the image data in step 82, as described above.

In step 86, the result 84 is used together with the preliminary priority value(s) to calculate position coverage weights. In step 88, gradient or surface normal coverage weights are calculated using the results 72 and 84 and, optionally, the position coverage weights calculated in step 86. One or a combination of steps 86 and 88 yields a weighting factor. For example, one or a combination of steps 86 and 88 yields one or more of the third weighting factor, the fourth weighting factor and the fifth weighting factor described above.

In step 90, the preliminary priority value(s) are weighted using one or more of the determined weighting factors. This weighting results in the (e.g., final) priority values of the at least one surface point. The at least one surface point may be classified into one of three distinct groups depending on the priority value. For example, a first group 92 comprises all surface points that are covered with already obtained registration points (e.g., have priority values of 0), a second group 94 comprises all surface points that are still to be covered by acquiring registration points and have low priority values (e.g., below a certain threshold but above 0), and a third group 96 comprises all surface points that are still to be covered by acquiring registration points and have high priority values (e.g., equal to or above the certain threshold).

In step 98, the visualization of the indication of the priority value of the at least one surface point is triggered to be displayed. This step may thus correspond to step 30 described with reference to FIG. 2. The visualization may comprise a three-dimensional visualization provided for the user, e.g., a representation of the skin surface with the indication of the priority value of the at least one surface point. The visualization may comprise a visualization of a patient image comprised in the image data. Indications of priority values of each of the surface points defining the skin surface in the image data may be visualized. The at least one surface point may be displayed in accordance with a display attribute associated with the group into which the at least one surface point is classified. Alternatively or additionally, each surface point may be represented in accordance with a display attribute determined only based on the priority value of the at least one surface point (e.g., irrespective of the groups).

In the following, examples of the non-patient specific virtual mask 38, the image 35 comprised in the image data, the matched virtual mask and the visualization of the indication of the priority of the at least one surface point will be described with reference to FIGS. 7 to 11.

FIG. 7 shows two exemplary illustrations of the non-patient-specific virtual mask 38 in accordance with the present disclosure. Both illustrations are examples of non-patient specific virtual masks 38 formed as meshes comprising mesh nodes 40. The faces illustrated in the background represent a generic human face and are not determined based on or described by the image data of the patient. A geometry (e.g., an area and a contour) of the virtual mask 38 may be defined by a predetermined coverage area 41 that is for example defined by at least some of the mesh nodes 40 and at least some of the lines 42 connecting the mesh nodes 40. In one example, the virtual mask is formed as the mesh, wherein each mesh line 42 has an associated thickness defining the coverage area 41. In another example, the virtual mask is formed as the mesh, wherein any point on the mesh lines 42 defines an area of the virtual mask, the area being circular and having a preset radius, and the sum of all areas forming the coverage area 41.

The left illustration is an example of a non-patient specific virtual mask 38 selected in case the bone surface is known and/or can be determined based on the image data. The right illustration is an example of a non-patient specific virtual mask 38 selected in case the bone surface is not known and/or cannot be determined based on the image data.

As can be seen, one of the mesh nodes 40 in the left example is an anchor point associated with a nose tip as anatomical landmark. The corresponding mesh node 40 in the right example is not associated with the nose tip as anatomical landmark. Other mesh nodes 40 in both examples are anchor points associated with an endocanthion or an exocanthion. In the left example, the mesh forming the non-patient specific virtual mask 38 comprises a line 42 connecting the anchor points associated with the endocanthion and the exocanthion, which is not the case in the right example.

Figure 8:
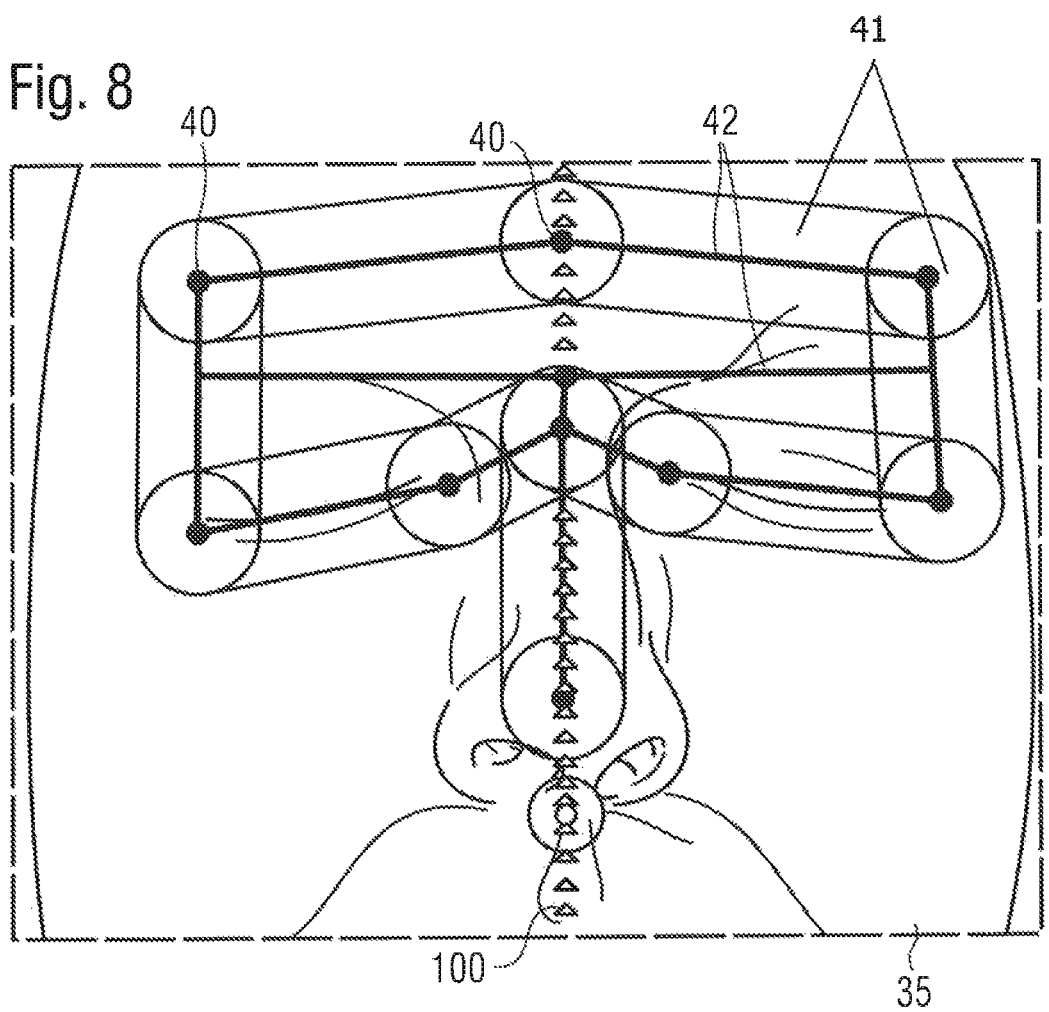
FIG. 8 shows an exemplary illustration of a matched virtual mask in accordance with the present disclosure.

FIG. 8 shows an exemplary illustration of the matched virtual mask in accordance with the present disclosure. In this example, the non-patient-specific virtual mask 38 as shown in the left illustration of FIG. 7 has been matched to image data of a patient. The matched virtual mask is in this example illustrated overlaid on the patient image 35. It can be seen that the positions of the mesh nodes 40 corresponding to the anchor points have been adjusted based on the landmarks in the image data. This becomes especially apparent when comparing the orientation of the mesh lines 42 connecting the anchor points associated with the endocanthion and the exocanthion between FIGS. 7 and 8. A symmetry plane 100 is also indicated in the illustration of FIG. 8. The symmetry plane 100 in this example is the sagittal plane. It can be seen that four anchor points 44 of the matched virtual mask lie within the symmetry plane 100. For these four anchor points 44, the associated anatomical landmark may correspond to the sagittal plane.

Figure 9:
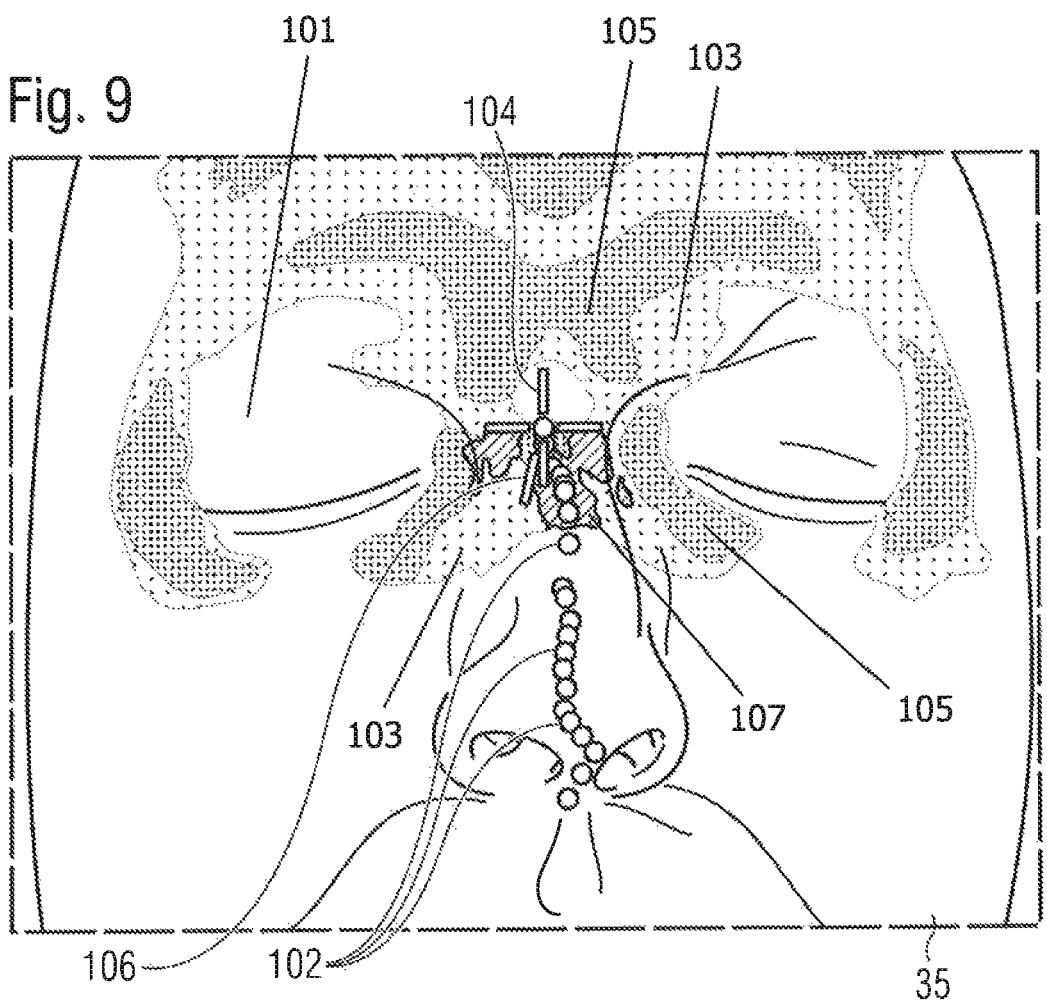
FIG. 9 shows an exemplary illustration of a visualization of priority values of different surface points in accordance with the present disclosure.

FIG. 9 shows an exemplary illustration of a visualization of priority values of different surface points in accordance with the present disclosure. The priority values may be determined based on the virtual mask shown in FIG. 8. The view shown in FIG. 9 may be triggered to be displayed on the display 6 in step 30 or 98. That is, the visualization triggered to be displayed may comprise a representation of the patient image 35 including the skin surface, and a visualization of priority values of different (e.g., all) surface points.

The priority value of the at least one surface point may be visualized by displaying a part of the skin surface at the position of the at least one surface point with a certain color. In the shown example, a higher priority value is indicated with a (e.g., white) color and higher opaqueness. On the other hand, a lower priority value is indicated with a (e.g., same or different) color and lower opaqueness.

In the example of FIG. 9, priority values of surface points in a first region 101 are the lowest. In this case, the priority values of the surface points in the first region 101 are indicated by not highlighting or otherwise changing the appearance of the patient image 35 in the first region 101. In other words, the first region(s) 101 may inform the user where on the patient's body no additional registration points are required.

In difference thereto, priority values of surface points in second regions 103 are higher than the priority values of the surface points in the first region 101. In the shown example, the priority values of the surface points in the second regions 103 are indicated by highlighting the second regions 103 in the patient image 35 with a first optical property (e.g., with a first color overlaid onto the patient image 35 and having a first opaqueness). The surface points in the second regions 103 may fall into the class 94. In other words, the second regions 103 may inform the user where to acquire somewhat useful registration points on the patient's body.

Still further, priority values of surface points in third regions 105 are higher than the priority values of the surface points in the second regions 103. In the shown example, the priority values of the surface points in the third regions 105 are indicated by highlighting the third regions 105 in the patient image 35 with a second optical property different from the first optical property (e.g., with the first color overlaid onto the patient image 35 and having a second opaqueness higher than the first opaqueness). The surface points in the third regions 105 may fall into the class 96. In other words, the third regions 105 may inform the user where on the patient's body additional registration points are urgently required.

As described herein, the individual surface points in the different regions 101, 103 and 105 have different priorities because the priority values may be determined by weighting the assigned or preliminary priority values with at least one of the first weighting factor (e.g., based on a distance between the skin surface and the bone surface) and the second weighting factor (e.g., based on an elasticity of body tissue underneath the skin or body surface). Furthermore, priority values of surface points remote from the registration region (e.g., on the cheeks) are lower compared with priority values of surface points close to or inside the registration region (e.g., next to the exocanthion). This may be because the priority values are determined depending on a position of the surface points relative to the registration area, for example as described above with reference to step 70 or FIG. 4. The priority values of the surface points may be affected by the determined positions of the obtained registration points. For example, as described above, the third or the fourth weighting factor may be used to determine the priority values upon obtaining the registration points.

Priority values of surface points that are significantly affected by the obtained registration points, i.e., that are reduced more than a predefined amount upon determining the positions of the obtained registration points in the coordinate system of the image data and updating the priority values (e.g., using one or more of the third to fifth weighting factors), may be indicated differently than other priority values. In the shown example, such significantly affected priority values of surface points in fourth regions 107 are indicated by highlighting the fourth regions 107 in the patient image 35 with a third optical property different from at least one of the first and the second optical property (e.g., with a second color different from the first color, overlaid onto the patient image 35 and having a third opaqueness higher than at least one of the first and the second opaqueness). The surface points in the fourth regions 107 may fall into the class 92. In other words, the fourth regions 107 may inform the user which areas of the patient's body are already sufficiently covered with the obtained registration points.

As shown in FIG. 9, indications 102 of the determined positions of the obtained registration points may also be displayed. In this example, each of the determined positions of obtained registration points is indicated as a point in the image 35. In the exemplary illustration of FIG. 9, a virtual representation 104 of the registration probe 10 is also displayed. In particular, an indication of a position of the distal tip of the registration probe 10 relative to the patient's body 12 may be triggered to be displayed, for example as a pair of crosshairs overlaid onto the image 35 of the patient. An indication of the pose of the registration probe 10 relative to the patient's body 12 may be triggered to be displayed, for example as a line 106 representing a projection of an axis of the registration probe 10 into a viewing direction in which the image 35 is displayed.

Some regions of the skin surface are more suitable for acquiring a registration point than others. The visualization informs the user accordingly such that he is guided where on the patient's body 12 to acquire the registration points to be used for the registration between the patient's body 12 and the image data. The indications of acquired registration points and the current position or pose of the registration probe 10 further helps the user to identify where to move the registration probe 10 for acquiring additional registration points.

Figure 10:
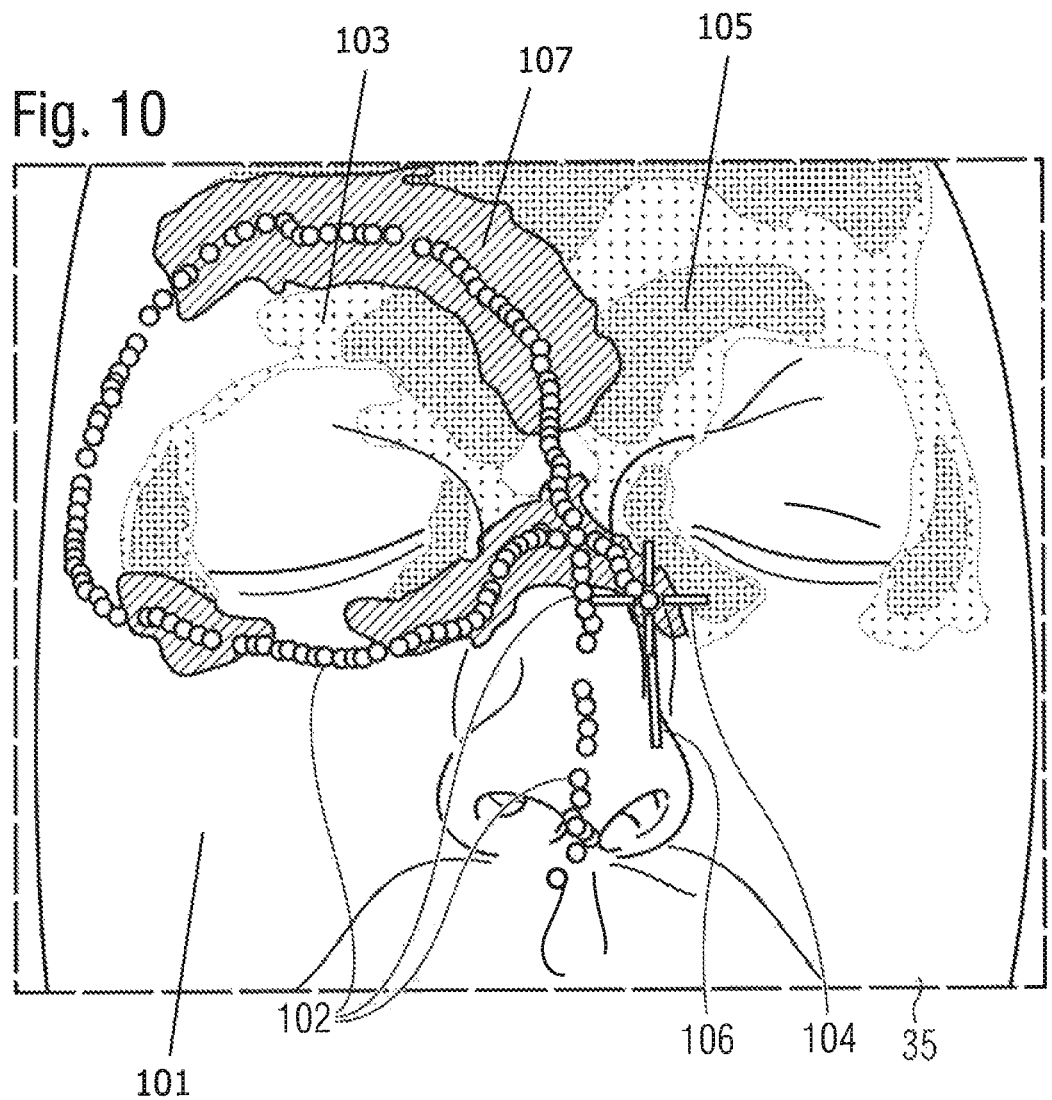
FIG. 10 shows an exemplary illustration of a visualization of priority values of different surface points in accordance with the present disclosure.

FIG. 10 shows an exemplary illustration of a visualization of priority values of different surface points in accordance with the present disclosure. In this case, a larger amount of registration points has been acquired (e.g., obtained) compared with FIG. 9. This results in an update of the priority values of the surface points due to a determination of the priority values using one or more of the third to fifth weighting factors that take into account a coverage of the skin surface with acquired registration points. It follows that the surface points, after having updated the priority values, may lie in another one of the first, second, third or fourth regions 101, 103, 105 and 107. One may say that the geometries of the first, second, third or fourth regions 101, 103, 105 and 107 are continually updated during registration point acquisition.

Generally speaking, the more registration points have been acquired within a given region of the skin surface, the lower may be the priority values of remaining surface points within this region. Priority values of surface points in areas having a homogeneous surface shape (e.g., the left forehead from the patient's perspective) become lower the more registration points are acquired in similarly shaped surface areas (e.g., the right forehead from the patient's perspective). Areas sufficiently covered with acquired registration points (e.g., comprising surface points falling into class 92) are visualized differently than other areas of the surface (e.g., comprising surface points falling into class 94 or 96). A registration point acquired on a flat surface portion covers a larger region of the skin surface compared with a registration points acquired on a bent surface portion. This is because the use of acquiring additional registration points on a flat surface portion next to an already acquired registration point is lower compared with the use of acquiring additional registration points on a bent surface portion next to an already acquired registration point.

FIG. 11 shows an exemplary illustration of a visualization of priority values of different surface points in accordance with the present disclosure. In this case, a larger amount of registration points has been acquired compared with FIG. 10. It can be seen that some areas of the skin surface that were highlighted for point acquisition in FIG. 9 are no longer of interest as their surface points have lower priority values (e.g., priority values of 0 such that these regions are no longer highlighted in the image 35). Some areas of the skin surface that were highlighted for point acquisition in FIG. 9 are still highlighted as their surface points still or now have high priority values. Again, one may say that the surface points, after having updated the priority values based on the additional obtained registration point(s), may lie in another one of the first, second, third or fourth regions 101, 103, 105 and 107. Put differently, the geometries of the first, second, third or fourth regions 101, 103, 105 and 107 may be updated after each obtained registration point.

In case an amount of surface points having a priority value above a given threshold falls below a preset amount, these surface points may be highlighted by using different indications than previously used for indicating high priorities. In the given example, this means that once the total area of the third regions 105 falls below a preset threshold, the surface points within the third regions 105 are highlighted differently than before. As an example, the priority values of the surface points in the third regions 105, after the total area of all third regions 105 falls below the preset threshold, are indicated by highlighting the third regions 105 in the patient image 35 with a fourth optical property different from the second optical property (e.g., with a third color overlaid onto the patient image 35 different from the first and the second color). Put differently, these remaining surface points in the third regions 105 may be specially highlighted using another color or opaqueness than previously used for indicating high priorities, or by applying a blinking pattern, to point the user's attention to the potentially small remaining surface areas to be covered by acquiring additional registration points.

It is noted that the examples shown in FIGS. 9 to 11 are for illustrative purposes only. It is not necessary to cluster the surface points into several classes or regions, or to highlight distinct regions of the patient image 35 homogeneously. For instance, the indication of the priority value of a given surface point may be visualized by choosing an opaqueness of a preset color overlaid onto the given surface point, wherein the opaqueness is correlated with (e.g., proportional to) the priority value of the given surface point. In other words, there may be a gradual visualization of the priority values. In one example, the priority values of surface points falling into a same of the first, second, third or fourth region 101, 103, 105, 107 are visualized using a same color, but also using a different opaqueness that is proportional to the individual priority values.

In summary, the present disclosure is directed to an advantageous technique of providing user guidance in surgical navigation. The non-patient-specific virtual mask and, optionally, the weighting factors are used to determine the priority value of the at least one surface point of the plurality of surface points defining the skin surface in the image data of the patient. The indication of the priority value is triggered to be displayed, informing the user about the priority of acquiring a registration point at a corresponding position on the patient's body. This helps the user in deciding where on the patient's body 12 to acquire one or more additional registration points using the registration probe 10 tracked by the tracking system 8. The registration point(s) acquired in accordance with the displayed indication may then be used to determine or update a registration between the patient's body 12 and the image data of the patient, allowing for an accurate navigation of surgical tools during a subsequent surgery.

The method disclosed herein may not comprise a surgical step. The method may in particular be computer-implemented and exclusively comprise steps of obtaining data, determining secondary data based on the obtained data, and triggering display of a visualization by outputting a trigger signal or output data. Tracking of the patient's body 12 may not require a substantial interaction with the body of a human. For example, the tracker may be temporarily attached onto a skin of the patient's body 12 using glue or a non-invasive attachment clamp attached to the tracker. The acquisition of the registration points may also not require a substantial interaction with the body of a human body. For example, a registration probe may be placed onto a skin of the patient's body 12 for acquiring the registration points.

The invention claimed is:

1. A computer-implemented method for guiding a surgeon to acquire one or more registration points on a body of a patient with a registration probe tracked by a tracking system, the method comprising:
   obtaining geometrical information defining relative positions between a non-patient-specific virtual mask and a plurality of anchor points, each of the plurality of anchor points being associated with a non-patient-specific anatomical landmark;
   obtaining, for each of the plurality of anchor points, a position of the associated non-patient-specific anatomical landmark in image data of the patient;
   matching the non-patient-specific virtual mask to the image data;
   obtaining a plurality of image surface points defining a skin surface in the image data;
   determining, based on the matched non-patient-specific virtual mask, for at least one of the plurality of image surface points, a priority value indicative of a priority for acquiring a registration point at a position, relative to the body, that corresponds to a position of the at least one of the plurality of image surface points relative to the skin surface defined in the image data; and
   triggering display of a visualization of the priority value of the at least one of the plurality of image surface points to facilitate a user determining whether to move the registration probe tracked by a tracking system to the position of the at least one of the plurality of surface points based on the priority value: and
   acquiring a registration point on the body of the patient with the registration probe positioned based on the priority value.

2. The method of claim 1, wherein the non-patient-specific virtual mask is matched to the image data by assigning, to each of the plurality of anchor points, the position of the associated non-patient-specific anatomical landmark in the image data and/or wherein the registration point is usable for a registration between the skin surface defined in the image data and the body of the patient based on the at least one of the plurality of image surface points and the registration point.

3. The method of claim 1, wherein the non-patient-specific virtual mask is formed as a multi-dimensional mesh comprising a plurality of mesh nodes, wherein each of the plurality of anchor points has a known position relative to one or more of the plurality of mesh nodes.

4. The method of claim 3, wherein each of the plurality of anchor points coincides with one of the plurality of mesh nodes.

5. The method of claim 1, wherein determining the priority value further comprises at least one of:
   assigning a first predefined priority value to the at least one of the plurality of image surface points if the at least one of the plurality of image surface points lies outside a registration area; and
   assigning a second predefined priority value to the at least one of the plurality of image surface points if the at least one of the plurality of image surface points lies inside the registration area, wherein the second predefined priority value is higher than the first predefined priority value,
   wherein the registration area is an area of the skin surface designated by the matched non-patient-specific virtual mask.

6. The method of claim 5, wherein the registration area is defined by a projection of the matched non-patient-specific virtual mask onto the skin surface.

7. The method of claim 5, further comprising selectively assigning the first predefined priority value to the at least one of the plurality of image surface points outside the registration area if the at least one of the plurality of image surface points is farther from the registration area than a predefined maximal distance.

8. The method of claim 7, wherein determining the priority value comprises, if the at least one of the plurality of image surface points lies outside the registration area and closer to the registration area than the predefined maximal distance, assigning an intermediate priority value smaller than the second predefined priority value and larger than the first predefined priority value to the at least one of the plurality of image surface points.

9. The method of claim 5, wherein determining the priority value comprises one of using the assigned predefined priority value as the priority value and weighting the assigned predefined priority value with one or more weighting factors to determine the priority value.

10. The method of claim 9, further comprising:
obtaining a bone surface of the patient's body;
determining a shortest distance between the at least one of the plurality of image surface points and the bone surface; and
determining a first weighting factor of the one or more weighting factors based on the determined shortest distance such that, the larger the shortest distance is, the lower is the weighting of the assigned predefined priority value of the at least one of the plurality of image surface points.

11. The method of claim 9, further comprising determining a second weighting factor of the one or more weighting factors based on an elasticity of body tissue underneath a body point lying on the patient's body such that, the higher the elasticity of the body tissue underneath the body point is, the lower is the weighting of the assigned predefined priority value of the at least one of the plurality of image surface points, wherein the body point has a position relative to the body corresponding to a position of the at least one of the plurality of image surface points relative to the skin surface.

12. The method of claim 9, further comprising determining a third weighting factor of the one or more weighting factors based on a second distance between a position of the at least one of the plurality of image surface points relative to the skin surface and a determined position of an obtained registration point relative to the skin surface, such that, the smaller the second distance is, the larger is the weighting of the assigned predefined priority value of the at least one of the plurality of image surface points.

13. The method of claim 9, further comprising determining a fourth weighting factor of the one or more weighting factors based on an angular difference between a first direction and a second direction, such that, the smaller the angular difference is, the lower is the weighting of the assigned predefined priority value of the at least one of the plurality of image surface points, wherein the first direction is defined by a shape of the skin surface at a position of the at least one of the plurality of image surface points relative to the skin surface, and the second direction is defined by a shape of the skin surface at a determined position of an obtained registration point relative to the skin surface.

14. The method of claim 9, further comprising:
determining a third weighting factor of the one or more weighting factors based on a second distance between a position of the at least one of the plurality of image surface points relative to the skin surface and a determined position of an obtained registration point relative to the skin surface, such that, the smaller the second distance is, the lower is the weighting of the assigned predefined priority value of the at least one of the plurality of image surface points; and
determining a fourth weighting factor of the one or more weighting factors based on an angular difference between a first direction and a second direction, such that, the smaller the angular difference is, the lower is the weighting of the assigned predefined priority value of the at least one of the plurality of image surface points, wherein the first direction is defined by a shape of the skin surface at a position of the at least one of the plurality of image surface points relative to the skin surface, and the second direction is defined by a shape of the skin surface at a determined position of an obtained registration point relative to the skin surface,
wherein the third weighting factor and the fourth weighting factor are determined for each of a plurality of determined positions of obtained registration points, a product of the third weighting factor and the fourth weighting factor is calculated for each of the plurality of determined positions of the obtained registration points, and the assigned predefined priority value is weighted with only the largest one of the calculated products.

15. The method claim 9, further comprising determining a fifth weighting factor of the one or more weighting factors based on a first direction and a plurality of second directions, such that, the more of a plurality of angular differences between the first direction and each of the plurality of second directions are within a predefined angular range, the lower is the weighting of the assigned predefined priority value of the at least one of the plurality of image surface points, wherein the first direction is defined by a shape of the skin surface at a position of the at least one of the plurality of image surface points relative to the skin surface, and wherein each second direction is defined by a shape of the skin surface at a determined position of one of a plurality of obtained registration points relative to the skin surface.

16. The method of claim 15, wherein the fifth weighting factor is further determined based on a third distance between the at least one of the plurality of image surface points and one of the plurality of obtained registration points having a second direction most similar to the first direction among the plurality of second directions, such that, the shorter the third distance is, the lower is the weighting of the assigned predefined priority value of the at least one of the plurality of image surface points.

17. The method of claim 16, wherein the second direction most similar to the first direction has, among angular differences between the first direction and each of the plurality of second directions, the smallest angular difference.

18. A data processing apparatus for guiding a surgeon to acquire one or more registration points on a body of a patient comprising:
a tracking system configured to track a registration probe; and
a processor configured to:
obtain geometrical information defining relative positions between a non-patient-specific virtual mask and a plurality of anchor points, each of the plurality of anchor points being associated with a non-patient-specific anatomical landmark;

obtain, for each of the plurality of anchor points, a position of the associated non-patient-specific anatomical landmark in image data of the patient;

match the non-patient-specific virtual mask to the image data;

obtain a plurality of image surface points defining a skin surface in the image data; determine, based on the matched non-patient-specific virtual mask, for at least one of the plurality of image surface points, a priority value indicative of a priority for acquiring a registration point at a position, relative to the body, that corresponds to a position of the at least one of the plurality of image surface points relative to the skin surface defined in the image data; and trigger display of a visualization of the priority value of the at least one of the plurality of image surface point to facilitate a user determining whether to move the registration probe tracked by a tracking system to the position of the at least one of the plurality of surface points based on the priority value; and acquire a registration point on the body of the patient with the registration probe positioned based on the priority value.

19. A non-transitory computer program product for guiding a surgeon to acquire one or more registration points on a body of a patient comprising instructions which, when executed by a processor, cause the processor to:

obtain geometrical information defining relative positions between a non-patient-specific virtual mask and a plurality of anchor points, each of the plurality of anchor points being associated with a non-patient-specific anatomical landmark;

obtain, for each of the plurality of anchor points, a position of the associated non-patient-specific anatomical landmark in image data of the patient;

match the non-patient-specific virtual mask to the image data;

obtain a plurality of image surface points defining a skin surface in the image data;

determine, based on the matched non-patient-specific virtual mask, for at least one of the plurality of image surface points, a priority value indicative of a priority for acquiring a registration point at a position, relative to a body of a patient, that corresponds to a position of the at least one of the plurality of image surface points relative to the skin surface defined in the image data; and trigger display of a visualization of the priority value of the at least one of the plurality of image surface points to facilitate a user determining whether to move the registration probe tracked by a tracking system to the position of the at least one of the plurality of surface points based on the priority value; and acquire a registration point on the body of the patient with the registration probe positioned based on the priority value.

\* \* \* \* \*